US008524499B2

(12) United States Patent
Goldman et al.

(10) Patent No.: US 8,524,499 B2
(45) Date of Patent: Sep. 3, 2013

(54) REGULATORY SEQUENCES THAT DIRECT GENE EXPRESSION TO SPINAL MOTOR NEURONS AND USES THEREOF

(75) Inventors: Steven A. Goldman, Webster, NY (US); Takahiro Nakano, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 280 days.

(21) Appl. No.: 10/984,406

(22) Filed: Nov. 9, 2004

(65) Prior Publication Data

US 2005/0129672 A1  Jun. 16, 2005

Related U.S. Application Data

(60) Provisional application No. 60/518,921, filed on Nov. 10, 2003.

(51) Int. Cl.
*C12N 15/86* (2006.01)
*C12N 15/12* (2006.01)
*C12N 15/00* (2006.01)

(52) U.S. Cl.
USPC ......... 435/456; 435/69.1; 435/368; 536/24.1; 424/93.2

(58) Field of Classification Search
None
See application file for complete search history.

(56) References Cited

U.S. PATENT DOCUMENTS

| | | | |
|---|---|---|---|
| 5,491,084 | A | 2/1996 | Chalfie et al. |
| 5,928,947 | A | 7/1999 | Anderson et al. |
| 6,060,310 | A | 5/2000 | Cho-Chung |
| 6,929,948 | B1 | 8/2005 | Smith et al. |
| 2002/0012903 | A1 | 1/2002 | Goldman et al. |
| 2002/0168338 | A1* | 11/2002 | Baird ........................... 424/93.2 |
| 2003/0118556 | A1* | 6/2003 | Kaspar et al. ................ 424/93.2 |
| 2004/0014210 | A1 | 1/2004 | Jessell et al. |
| 2004/0029269 | A1 | 2/2004 | Goldman et al. |
| 2005/0003544 | A1 | 1/2005 | Goldman et al. |
| 2005/0181503 | A1 | 8/2005 | Goldman et al. |
| 2005/0196864 | A1 | 9/2005 | Goldman et al. |

FOREIGN PATENT DOCUMENTS

WO  WO 03075647 A2 *  9/2003

OTHER PUBLICATIONS

Boillee S, Cleveland DW. Gene therapy for ALS delivers .Trends Neurosci. May 2004;27(5):235-8.*
Blits B, Bunge MB. Direct gene therapy for repair of the spinal cord.J Neurotrauma. Mar-Apr. 2006;23(3-4):508-20.*
Xiang S, Pan W, Kastin AJ. Strategies to create a regenerating environment for the injured spinal cord.Curr Pharm Des. 2005;11(10):1267-77.*
SejvarJJ and Marfin AA. Manifestations of West Nile neuroinvasive disease. Rev. Med. Virol. 2006;16:209-224.*
NCBI Entrez Nucleotide results for Accession No. 129977, Jan. 10, 2003. printed Jan. 10, 2008 pp. 1-28.*
NCBI Entrez Nucleotide results for Accession No. AC006357, Jan. 10, 2003. printed Oct. 3, 2008 pp. 1-2.*
Sanger Centre group et al. Toward a complete human genome sequence.Genome Res. Nov. 1998;8(11):1097-108.*
NCBI Entrez Nucleotide results for Accession No. AC128478. Sep. 22, 2002. printed Oct. 3, 2008 pp. 1-2.*
Russell, S. J., Replicating Vectors for Gene Therapy of Cancer: Risks, Limitations and Prospects, European J Cancer, 1994, vol. 30A (8), pp. 1165-1171.*
Thomas et al, Progress and Problems With the Use of Viral Vectors for Gene Therapy, Nature, 346 I May 2003, vol. 4, pp. 346-358.*
Check, E, Cancer fears cast doubts on future of gene therapy, Nature,2003, vol. 421, bottom of p. 678.*
Opalinska and Gewirtz, Nucleic-Acid Therapeutics: Basic Principles and Recent Applications, Nature Reviews, 2002, vol. 1, pp. 503-514.*
Federici et al, Gene-Based Treatment of Motor Neuron Disease, Muscle and Nerve, 2006, pp. 302-323.*
McClelland et al, Motor Neuron Inhibition—Based Gene Therapy for Spasticity, 2007, Am. J. Phys. Med. Rehabil. • vol. 86, No. 5, pp. 412-421.*
Aparicio et al., "Detecting Conserved Regulatory Elements with the Model Genome of the Japanese Puffer Fish, *Fugu rubripes*," *Proc. Natl. Acad. Sci. USA* 92:1684-1688 (1995).
Aparicio et al., "Whole-Genome Shotgun Assembly and Analysis of the Genome of *Fugu rubripes*," *Science* 297:1301-1310 (2002).
Arber et al "Requirement for the Homeobox Gene *Hb9* in the Consolidation of Motor Neuron Identity," *Neuron* 23:659-674 (1999).
Brenner et al., "Characterization of the Pufferfish (*Fugu*) Genome as a Compact Model Vertebrate Genome," *Nature* 366:265-268 (1993).
Briscoe et al., "A Homeodomain Protein Code Specifies Progenitor Cell Identity and Neuronal Fate in the Ventral Neural Tube," *Cell* 101:435-445 (2000).
Briscoe & Ericson, "Specification of Neuronal Fates in the Ventral Neural Tube," *Curr. Opin. Neurobiol.* 11:43-49 (2001).
Briscoe et al., "Homeobox Gene Nkx2.2 and Specification of Neuronal Identity by Graded Sonic Hedgehog Signalling," *Nature* 398:622-627 (1999).
Chan & Mann, "A Structural Model for a Homeotic Protein-Extradenticle-DNA Complex Accounts for the Choice of HOX Protein in the Heterodimer," *Proc. Natl. Acad. Sci. USA* 93:5223-5228 (1996).
Dasen et al., "Motor Neuron Columnar Fate Imposed by Sequential Phases of Hox-c Activity," *Nature* 425:926-933 (2003).

(Continued)

*Primary Examiner* — Maria Marvich
(74) *Attorney, Agent, or Firm* — LeClairRyan, a Professional Corporation

(57) ABSTRACT

The present invention relates to an enhancer which functions only in human brain and/or spinal cord motor neurons, where the enhancer comprises a nucleotide sequence of SEQ ID NO: 5, SEQ ID NO: 10, or SEQ ID NO: 16. The enhancer can be utilized as part of a nucleic acid construct which also has a nucleic acid encoding a marker protein or a therapeutic protein, a 3' control region, and, optionally, a basal promoter, where these components are positioned with respect to one another to permit expression of the marker protein or the therapeutic protein. The enhancer of the present invention is useful in a method of isolating an enriched or purified population of motor neurons from a mixed population of human brain and/or spinal cells. In addition, the enhancer of the present invention can be used in a method of therapeutically targeting motor neurons.

26 Claims, 7 Drawing Sheets

(56) References Cited

OTHER PUBLICATIONS

Di Rocco et al., "Functional Dissection of a Transcriptionally Active, Target-Specific Hox-Pbx Complex," *EMBO J.* 16:3644-3654 (1997).
Gage et al., "The *Bicoid*-Related Pitx Gene Family in Development," *Mammal. Genome* 10:197-200 (1999).
Gaunt et al., "Expression of the Mouse *Goosecoid* Gene During Mid-Embryogenesis May Mark Mesenchymal Cell Lineages in the Developing Head, Limbs and Body Wall," *Development* 117:769-778 (1993).
Goridis & Brunet, "Transcriptional Control of Neurotransmitter Phenotype," *Curr. Opin. Neurobiol.* 9:47-53 (1999).
Heinemeyer et al., "Databases on Transcriptional Regulation: Transfac, TRRD and Compel," *Nucleic Acids Res.* 26:362-367 (1998).
Helms et al., "Autoregulation and Multiple Enhancers Control *Math 1* Expression in the Developing Nervous System," *Development* 127:1185-1196 (2000).
Ho et al., "Site-Directed Mutagenesis by Overlap Extension Using the Polymerase Chain Reaction," *Gene* 77:51-59 (1989).
Hogan et al., Manipulating the Mouse Embryo, *Cold Spring Harbor Laboratory Press, Cold Spring Harbor* (1994) (Table of Contents only).
Jessell & Melton, "Diffusible Factors in Vertebrate Embryonic Induction," *Cell* 68:257-270 (1992).
Jessell, T.M., "Neuronal Specification in the Spinal Cord: Inductive Signals and Transcriptional Codes," *Nat. Rev. Genet.* 1:20-29 (2000).
Jungbluth et al., "Specification of Distinct Motor Neuron Identities by the Singular Activities of Individual *Hox* Genes," *Development* 126:2751-2758 (1999).
Lee et al., "Analysis of Embryonic Motoneuron Gene Regulation: Depression of General Activators Function in Concert with Enhancer Factors," *Development* 131:3295-3306 (2004).
Lee & Pfaff, "Synchronization of Neurogenesis and Motor Neuron Specification by Direct Coupling of bHLH and Homeodomain Transcription Factors," *Neuron* 38:731-745 (2003).
Levy et al., "Retroviral Transfer and Expression of Humanized, Red-Shifted Green Fluorescent Protein Gene Into Human Tumor Cells," *Nature Biotechnol.* 14:610-614 (1996).
Liu et al., "Assigning the Positional Identity of Spinal Motor Neurons: Rostrocaudal Patterning of Hox-c Expression by FGFs, Gdf1 1, and Retinoids," *Neuron* 32:997-1012 (2001).
Lumsden & Krumlauf, "Patterning the Vertebrate Neuraxis," *Science* 274:1109-1115 (1996).
Maconochie et al., "Cross-Regulation in the Mouse *HoxB* Complex: The Expression of *Hoxb2* in Rhombomere 4 is Regulated by *Hoxb1*," *Genes Dev.* 11:1885-1895 (1997).
Muhr et al., "Groucho-Mediated Transcriptional Repression Established Progenitor Cell Pattern and Neuronal Fate in the Ventral Neural Tube," *Cell* 104:861-873 (2001).
Müller et al., "Search for Enhancers: Teleost Models in Comparative Genomic and Transgenic Analysis of *cis* Regulatory Elements," *Bioessays* 24:564-572 (2002).
Ovitt et al., Microinjection and Trangenesis, pp. 427-437 (1997).
Pierani et al., "Control of Interneuron Fate in the Developing Spinal Cord by Progenitor Homeodomain Protein Dbxl," *Neuron* 29:367-384 (2001).
Quandt et al., "MatInd and MatInspector: New Fast and Versatile Tools for Detection of Consensus Matches in Nucleotide Sequence Data," *Nucleic Acids Res.* 23:4878-4884 (1995).
Roy et al., "Telomerase Immortalization of Neuronally Restricted Progenitor Cells Derived from the Human Fetal Spinal Cord," *Nat. Biotechnol.* 22:297-305 (2004).
Sambrook et al., Molecular Cloning: A Laboratory Manual, 2d Edition, Cold Spring Harbor Laboratory Press, Cold Spring Harbor, New York (1989).
Simeone et al., "A Vertebrate Gene Related to *Orthodenticle* Contains Homeodomain of the *Bicoid* Class and Demarcates Anterior Neuroectoderm in the Gastrulating Mouse Embryo," *EMBO J.* 12:2735-2747 (1993).
Simmons et al., "*Neurogenin2* Expression in Ventral and Dorsal Spinal Neural Tube Progenitor Cells is Regulated by Distinct Enhancers," *Dev. Biol.* 229:327-339 (2001).
Tanabe et al., "Specification of Motor Neuron Identity by the MNR2 Homeodomain Protein, " *Cell* 95:67-80 (1998).
Thaler et al., "Active Suppression of Interneuron Programs Within Developing Motor Neurons Revealed by Analysis of Homeodomain Factor HB9," *Neuron* 23:675-687 (1999).
Tiret et al., "Increased Apoptosis of Motoneurons and Altered Somatotopic Maps in the Brachial Spinal Cord of *Hoxc-8*-Deficient Mice," *Development* 125:279-291 (1998).
Vallstedt et al., "Different Levels of Repressor Activity Redundant and Specific Roles to *Nkx6* Genes in Motor Neuron and Interneuron Specification," *Neuron* 31:743-755 (2001).
Vult Von Steyern et al., "The Homeodomain Transcription Factors Islet 1 and HB9 Are Expressed in Adult Alpha and Gamma Motoneurons Identified by Selective Retrograde Tracing," *Eur. J. Neurosci.* 11:2093-2102 (1999).
Wichterle et al., "Directed Differentiation of Embryonic Stem Cells Into Motor Neurons," *Cell* 110:385-397 (2002).
Yee & Rigby, "The Regulation of Myogenin Gene Expression During the Embryonic Development of the Mouse," *Genes Dev.* 7:1277-1289 (1993).
Romano, Drug News Perspect 16(5):267-276 (2003).
Du et al., Stem Cells Dev. 13(4):372-81 (2004).
Li et al., Nat Siotechnol. 23(2)215-21 (2005).
Keyoung et al., Nat Biotechnology 19(9):843-50 (2001).
Yoshida et al., Cell Transplantation 8:427-430 (1999).
Sumitran et al., Cell Transplantation 8:601-610 (1999).
Barker et al., The Journal of Neuroscience 20(9):3415-3424 (2000).
Armstrong et al., Neuroscience 106(1):201-216 (2001).
Larsson et al., Brain Research Bulletin 49(5):367-376 (1999).
Larsson et al., Experimental Neurology 172:100-114 (2001).
Loseva et al., Brain Research 915:125-132 (2001).
Larsson et al., Scand. J. Immunol. 52:249-256 (2000).
Bjorklund et al., Nature Neuroscience 3(6):537-544 (2000).
Cao et al., Gene Therapy 8:1357-1362 (2001).
Schuldiner et al., Brain Research 913:201-205 (2001).
Roy et al., Nature Medicine 6(3):271-277 (2000).
Roy et al., Experimental Neurology 196:224-234 (2005).

* cited by examiner

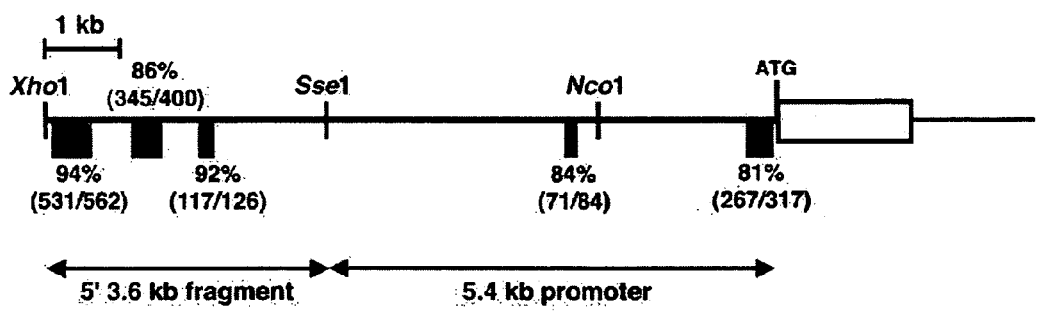
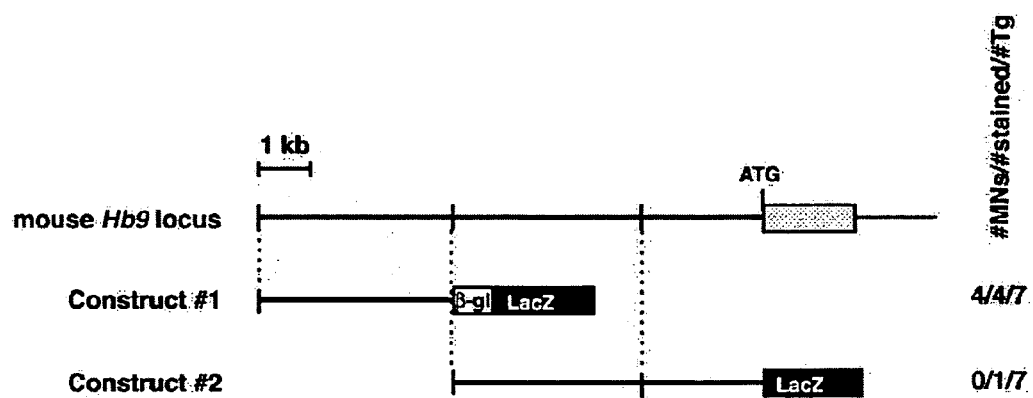
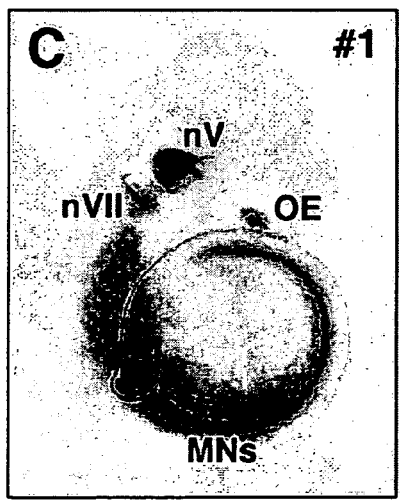
Figures 1A-D

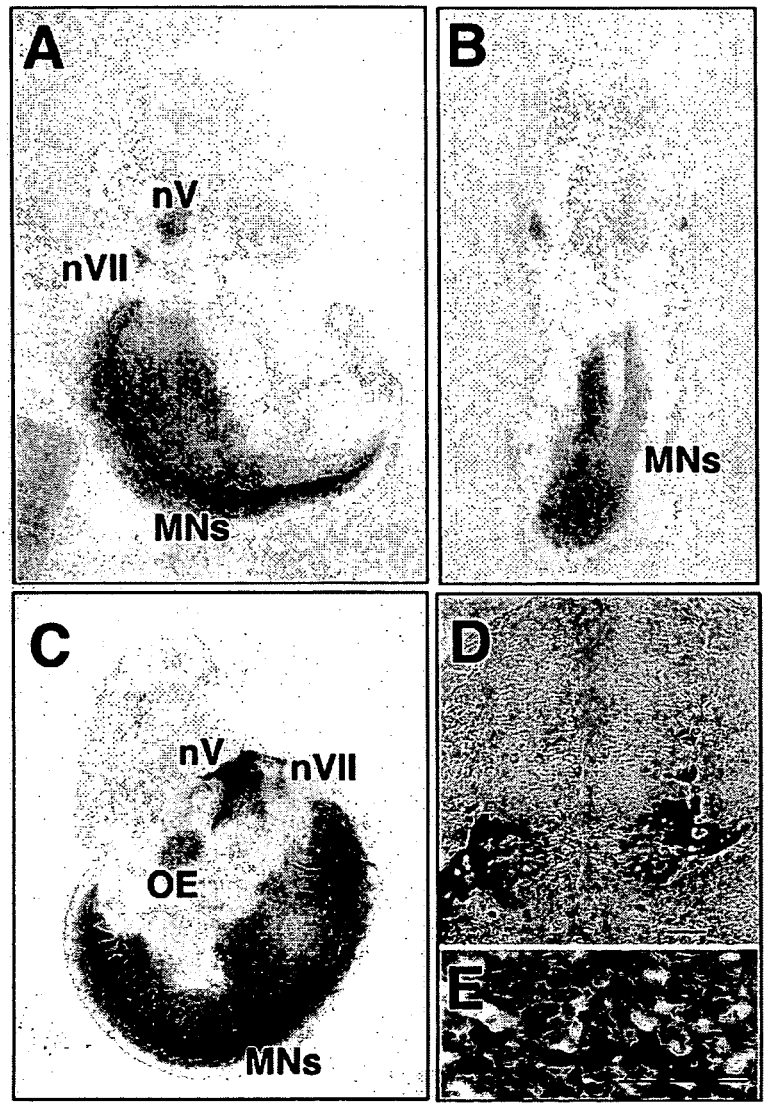
Figures 2A-E

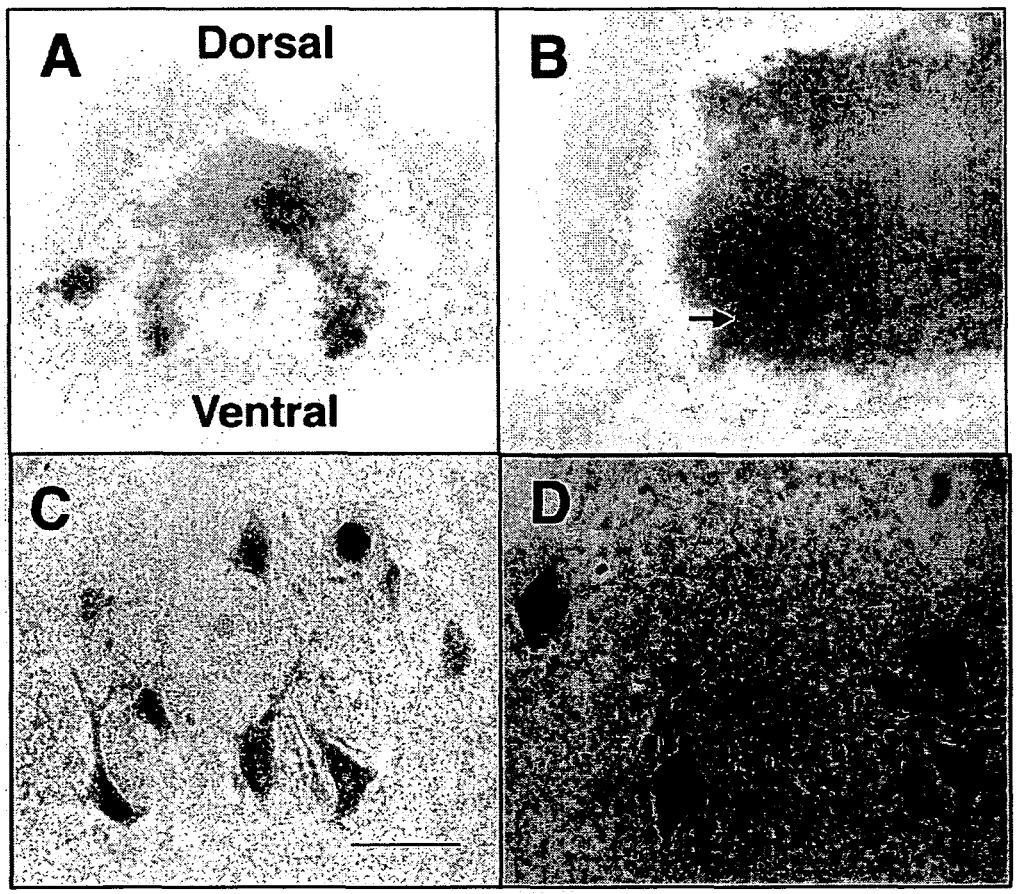
Figures 3A-D

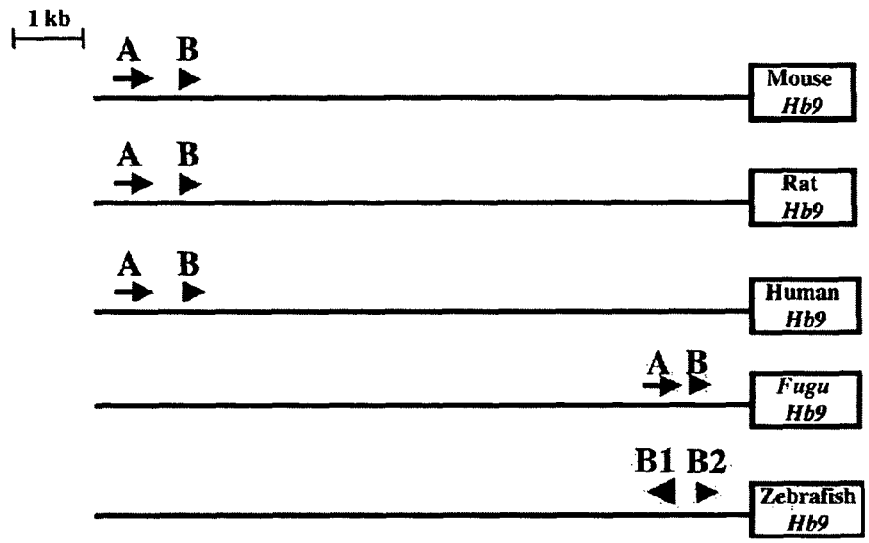
Figures 4A-C

D

```
Mouse      TGAATAAATTTAA-GCAGGCTAATTAATATATAAACTAGCTCAATTTGTCAAGTTGATTT
Rat        .............-..........................C..................
Human      .............-.GG.......................C..................
Fugu       .TC...CC...TCC.G.A.G..........T.......TTC.G........CT.......

Mouse      GTATTTTAGTTAATTGTGAAAGTAATTACCACATGGTCAAATTAACAGCTTTCTGGAAAT
Rat        ............................................................
Human      ............................................................
Fugu       ..........A..........T.........----G.AG................A....-

Mouse      GACCAAGCCTGAGGTTTTATTTCCTTCCTGGGTGAAGAAAATTCATTTTTCCAAGCTCTT
Rat        ............................................................
Human      ............................................................
Fugu       ....GG.TTCTG..G.CCGGG...A..TGA..C.CCTT.----.T.A.....TCTC.AA.A Mouse      GATGTGATGAATAAAAGTCATAAATCTGGGTGATTGGTGCAGGCAGAGTCTAAATGGCTT
Rat        ............................................................
Human      ............................................................
Fugu       .C..........A.GGG.CG...............C....A.....CA.TA..........C Mouse      CATATTTCATTTTAGGTTTAATAGAAATATTCATGCTC--TGTTTTAATGAAATTAAATT
Rat        ......................................--....................
Human      ......................................--....................
Fugu       .........CCGCT.C....................GGGACACC...............CC Mouse      GAAGGGGGATGGGGCT
Rat        ................C
Human      ................C
Fugu       .GC..AA.GC.CA---
```

E

```
Mouse      AGAGTGGTTAGCTGATGAATTGACAAAAACTAATCAGCTTTATTGGGAAACAGGTTTAAG
Rat        .....A..................................................... 
Human      ............................................................-..
Fugu       ..C.C.C....T......C.........................T.G........-..
Zebrafish  ...............GG...........C...............T.G........-...

Mouse      GGCACGGACGTGTCAATAACGCTCAGCCTGACCCCCTCTTCCATTAGCT-AGGCAGGCTG
Rat        ......G.........................................-..........
Human      ......G..........T.............G..........C................
Fugu       ....ACTGG..........TT....TTT.....T.............A..TTAAGT....T
Zebrafish  ....ACAGA..........TT....TC......T.T.TC..........T.AAG.....T Mouse      ATTAGA
Rat        ......
Human      ......
Fugu       ......
Zebrafish  ..A...
```

Figures 4D-E

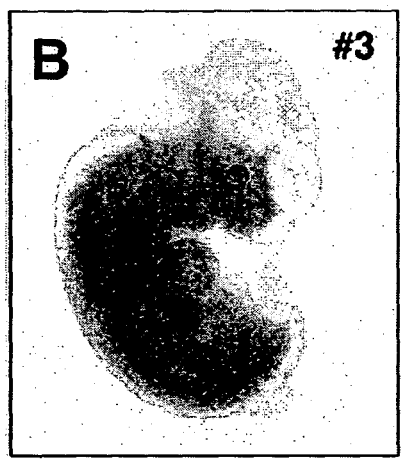
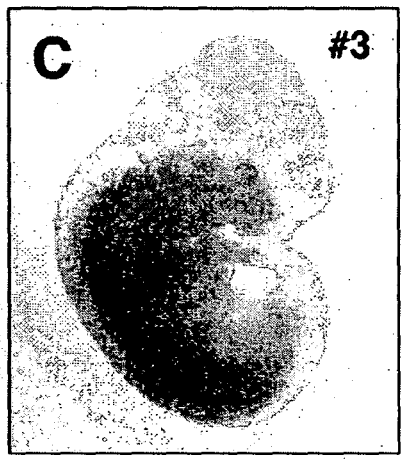
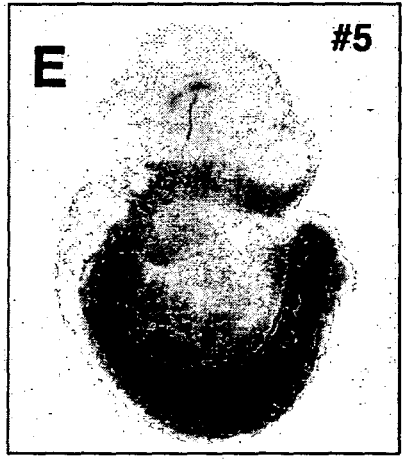
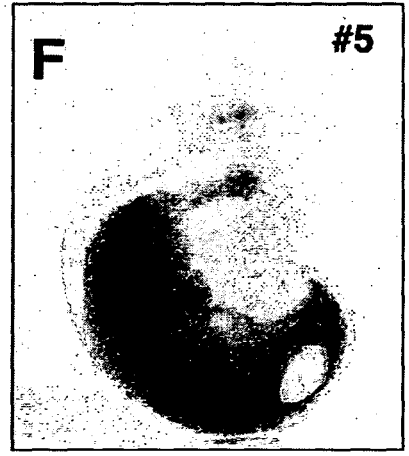
Figures 5A-G

A
```
Hox/Pbx consensus    TGATNNAT
    Construct #5    (TGATGAATTGACAAAAACTAATCA)
    Construct #6    (..CG..CG...........G..CG.)
```
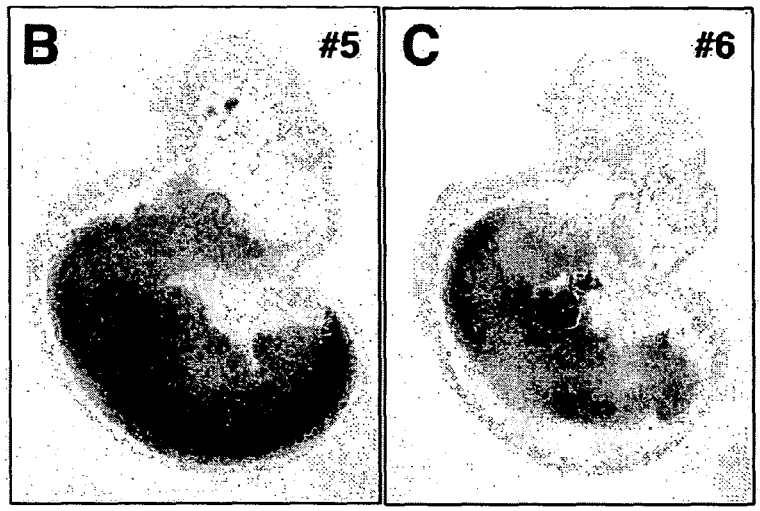
D
```
Wild-type oligo   5'-GTACGTTAGCTGATGAATTGACAAAAACTAATCAGCTTTA-3'
Mutant oligo      5'-...........CG..CG...........G..CG.......-3'
```
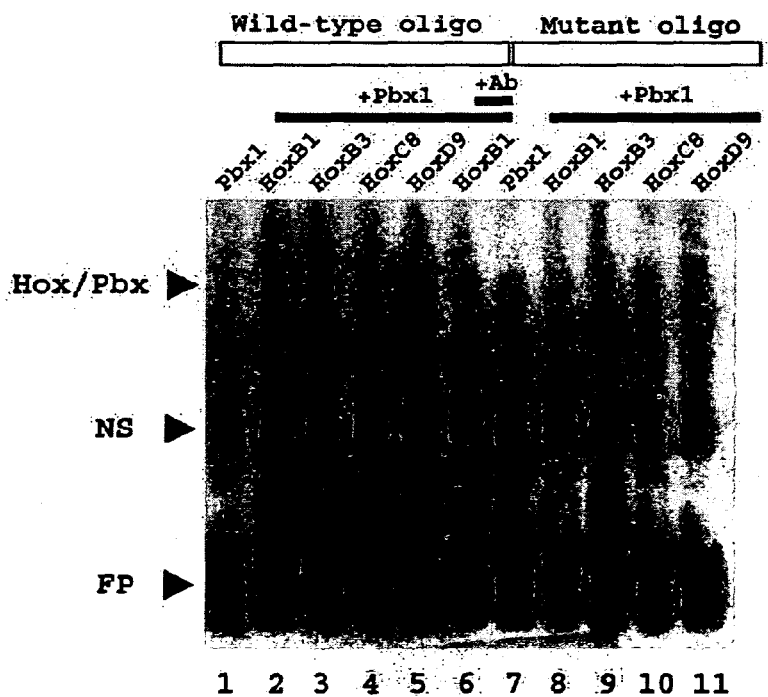
Figures 6A-D

REGULATORY SEQUENCES THAT DIRECT GENE EXPRESSION TO SPINAL MOTOR NEURONS AND USES THEREOF

This application claims the benefit of U.S. Provisional Patent Application Ser. No. 60/518,921, filed Nov. 10, 2003.

The subject matter of this application was made with support from the United States Government under The National Institute of Neurological Disorders and Stroke Grant No. R01NS33106 and NIH T32. The U.S. Government may have certain rights.

FIELD OF THE INVENTION

The present invention relates to an enhancer which functions only in human brain and/or spinal cord motor neurons as well as the incorporation of the enhancer in a nucleic acid construct and its use in a method of isolating an enriched or purified population of motor neurons from a mixed population of human brain and/or spinal cells or a method of therapeutically targeting motor neurons.

BACKGROUND OF THE INVENTION

The homeobox gene Hb9 is expressed selectively by motor neurons (MNs) in the developing CNS. Previous studies have identified a 9 kb 5' fragment of the mouse Hb9 gene that is sufficient to direct gene expression to spinal MNs in vivo.

In the vertebrate CNS, the specification of neural identity is initiated by humoral inductive factors, that impose a specific profile of transcription factor expression on neural progenitor cells, thereby restricting their phenotypic differentiation (Jessell et al., Cell 68:257-70 (1992), Goridis et al., Curr Opin Neurobiol 9:47-53 (1999)). In the developing spinal neuroepithelium, motor neuron (MN) progenitors arise in part in response to the ventralizing action of Sonic hedgehog (Shh) (Briscoe et al., Curr Opin Neurobiol 11:43-9 (2001)). The specification of MN progenitors by Shh is mediated through the patterned expression of homeodomain (HD) and basic helix-loop-helix (bHLH) transcription factors; these function primarily as transcriptional repressors (Muhr et al., Cell 104: 861-73 (2001)), whose cross-regulatory interactions establish distinct progenitor domains (Briscoe et al., Nature 398: 622-7 (1999); Briscoe et al., Cell 101:435-45 (2000); Jessell, Nat Rev Genet 1:20-9 (2000); Vallstedt et al., Neuron 31:743-55 (2001)). Through this general scheme, MN progenitors are restricted to a narrow region of the ventral neural tube termed the pMN domain (Briscoe et al., Cell 101:435-45. (2000); Jessell, Nat Rev Genet 1:20-9 (2000); Pierani et al., Neuron 29:367-84 (2001)) Within this domain, MN progenitors are characterized by two HD proteins, Nkx6.1 and Pax6, and a bHLH protein, Olig2. Together, these proteins serve to initiate the expression of distinct MN transcription factors, which include the HD protein HB9.

HB9 is expressed selectively by post-mitotic spinal MNs in the developing vertebrate CNS, and serves as a marker for the MN phenotype (Tanabe et al., Cell 95:67-80 (1998), Arber et al., Neuron 23:659-74 (1999)). Genetic studies in mice have suggested its importance in the consolidation and maintenance of MN identity (Arber et al., Neuron 23:659-74 (1999), Thaler et al., Neuron 23:675-87 (1999)). A 5' 9 kb Hb9 promoter has been shown to drive MN-specific expression in vivo (Arber et al., Neuron 23:659-74 (1999), Wichterle et al., Cell 110:385-397 (2002)). Nonetheless, the regulatory control of Hb9 gene expression is only poorly understood.

The present invention is directed to overcoming this deficiency in the art.

SUMMARY OF THE INVENTION

One aspect of the present invention relates to a method of isolating an enriched or purified population of motor neurons from a mixed population of human brain and/or spinal cells. This involves providing a mixed population of human brain and/or spinal cord cells comprising motor neurons and providing an enhancer which functions only in motor neurons, where the enhancer comprises a nucleotide sequence of SEQ ID NO: 5, SEQ ID NO: 10, or SEQ ID NO: 16. The nucleic acid molecule encoding a marker protein under control of the enhancer is introduced into the mixed population of human brain and/or spinal cord cells comprising motor neurons. Only the motor neurons are allowed to express the marker protein. The cells expressing the marker protein are separated from the mixed population of human brain and/or spinal cord cells comprising motor neurons. As a result, an enriched or purified population of motor neurons is isolated.

Another aspect of the present invention relates to an enhancer which functions only in human brain and/or spinal cord motor neurons, where the enhancer comprises a nucleotide sequence of SEQ ID NO: 5, SEQ ID NO: 10, or SEQ ID NO: 16.

Another embodiment of the present invention relates to an isolated nucleic acid construct which includes an enhancer which functions only in human brain and/or spinal cord motor neurons. The enhancer comprises a nucleotide sequence of SEQ ID NO: 5, SEQ ID NO: 10, or SEQ ID NO: 16. The construct also has a nucleic acid encoding a marker protein and a 3' control region, where the enhancer, the nucleic acid encoding a marker protein, and the 3' control region are positioned with respect to one another to permit expression of the marker protein.

A further aspect of the present invention relates to an isolated nucleic acid construct which includes an enhancer which functions only in human brain and/or spinal cord motor neurons, a basal promoter, a nucleic acid encoding a therapeutic protein, and a 3' control region. The enhancer comprises a nucleotide sequence selected from the group consisting of SEQ ID NO: 5, SEQ ID NO: 10, and SEQ ID NO: 16. The enhancer, the basal promoter, the nucleic acid encoding a therapeutic protein, and the 3' control region are positioned with respect to one another to permit expression of the therapeutic protein.

Also encompassed by the present invention is a method of therapeutically targeting motor neurons. This method involves providing a viral vector comprising the nucleic acid construct of the immediately preceding paragraph and administering the viral vector under conditions effective to infect motors neurons. As a result, the motor neurons are therapeutically targeted.

Here, discrete MN-specifying elements are identified, using homology searches between genomic sequences of evolutionary distant species. Based on homology screening of the mouse and human Hb9 promoters, a 3.6 kb Hb9 enhancer was identified that proved sufficient to drive MN-specific lacZ expression. It was then compared with mouse, human, and pufferfish (Fugu rubripes) genomic sequences, and a conserved 438 bp sequence, consisting of noncontiguous 313 bp and 125 bp fragments, residing within the 3.6 kb Hb9 enhancer was identified. The zebrafish (Danio rerio) Hb9 genomic region was then found to have two identical copies of the 125 bp sequence, but no counterpart for the 313 bp sequence. Transgenic analysis showed that the 125 bp alone was both necessary and sufficient to direct spinal MN-specific lacZ expression, whereas the 313 bp sequence had no such enhancer activity. Moreover, the 125 bp Hb9 enhancer was found to harbor two Hox/Pbx consensus binding sequences, mutations of which completely disrupted thoracolumbar Hb9 expression. These data suggest that Hox/Pbx plays a critical role in the segmental specification of spinal MNs. Together, these results indicate that the molecular pathways regulating Hb9 expression are evolutionarily conserved, and that MN-specific gene expression may be directed and achieved using a small 125 bp 5' enhancer.

In this study, applicants sought to identify cis-acting regulatory elements of the Hb9 gene specifically active in MNs, so as to predict factors that might regulate MN induction. Using cross-species homology analysis with enhancer screening by transgenesis, a highly conserved 125 bp cis-acting regulatory sequence was identified, which appears to direct gene expression to spinal MNs. Moreover, by site-directed mutagenesis, it was found that disrupting Hox/Pbx binding sites within this 125 bp Hb9 enhancer completely abolished β-gal expression in the thoracic and lumber spinal cord, without affecting the reporter gene expression in the cervical levels cord. Thus, 5' 9kn Hb9 promoter harbors a highly conserved 125 bp element that directs vertebrate MN gene expression, and Hox/Pbx binding sites within it appear to be necessary for thoracolumbar MN specification.

BRIEF DESCRIPTION OF THE DRAWINGS

FIGS. 1A-D show a 5' 3.6 kb fragment within 9 kb Hb9 promoter regulates Hb9 gene expression. FIG. 1A is a diagram of the Hb9 locus representing the Hb9 coding region (open box) and highly conserved sequences between the human and mouse Hb9 loci (red box). The number and percentage of conserved nucleotides are shown. Scale bar=1 kb. The position of the two fragments (3.6 kb and 5.4 kb) used to analyze gene expression activity in the Hb9 region is indicated. FIG. 1B shows transgenic constructs used to study the gene expression activity. Statistical overview of transgenic embryos is indicated. The transgenic embryos carrying construct #1, but not #2, showed the virtually same spinal β-gal expression pattern with ones carrying MN-specific 9 kb Hb9 promoter. β-gl, β-globin basal promoter in the BGZA reporter construct. FIGS. 1C and 1D show representative pictures of E10.5 whole-mount stained embryos containing construct #1 (FIG. 1C) and #2 (FIG. 1D), respectively. OE, olfactory epithelium; nV, trigeminal nerve; nVII, facial nerve; MNs, spinal motor neurons.

FIGS. 2A-E show transgene expression in whole-mount mouse embryos. FIGS. 2A-C show β-galactosidase (β-gal) staining in E10 (FIGS. 2A and B) and E11 (FIG. 2C) transgenic embryos. FIGS. 2A and C show lateral views, while FIG. 2B shows a dorsal view. FIG. 2D shows a cross-section of E10.5 thoracic spinal cord β-gal expression in the ventral side of the spinal cord and extending axons. FIG. 2E shows a coronal section immuno-stained for Islet-1. OE, olfactory epithelium; nV, trigeminal nerve; nVII, facial nerve; MNs, spinal motor neurons.

FIGS. 3A-D show expression patterns of reporter genes in the adult spinal cord. FIGS. 3A and B show β-gal expressions in representative adult thoracic spinal cord of a 12-week adult transgenic mouse carrying the construct #1. β-gal expressions were located in the ventral horn. The arrow indicates extending axons. FIG. 3C shows a transverse section of an adult spinal cord. The β-gal activity was restricted to neurons with large cell bodies in the ventral side of spinal, suggesting they are motor neurons. FIG. 3D shows the ChAT immunoreactivity (arrowheads) was co-localized with β-gal activity.

FIGS. 4A-E show the identification of evolutionarily conserved upstream genomic sequences among vertebrate Hb9 genes. FIG. 4A is a schematic view of the Hb9 genomic region showing the positions and directions of the two highly homologous regions, namely 313 bp fragment A and 125 bp fragment B, of the mouse, rat, human, pufferfish, and zebrafish. B1 and B2 indicate two identical copies of the 125 bp sequence found in zebrafish. FIG. 4B shows a comparison of the deduced amino acid sequences of the mouse Hb9 (MmHb9), rat Hb9 (RnHb9), human Hb9 (HsHb9), Fugu Hb9 (FrHb9), zebrafish Hb9 (DrHb9) (SEQ ID NOs: 29-33, respectively) in the vicinity of the homeodomains. Perfectly conserved homeodomains among all listed species are shaded. FIG. 4C shows the degree of sequence identity of the 313 bp region A and 125 bp region B among evolutionary distinct species. FIGS. 4D and E show alignment of the 313 bp region A (FIG. 4D) (SEQ ID NOs: 7, 8, 6, and 9, respectively) and 125 bp region B (FIG. 4E) (SEQ ID NOs: 12, 13, 11, and 14, respectively) from mouse, rat, human, and Fugu using the Clustral algolisum. Two Hox/Pbx consensus binding sequences (TGATNNAT) within the 125 bp are shaded.

FIGS. 5A-G show the functional characterization of the two evolutionarily sequences. FIG. 5A shows constructs and statistical overview of transgenic embryos. A, 313 bp region A; B, 125 bp region B. FIGS. 5B-E show expression patterns of reporter genes in representative transgenic embryos. FIGS. 5B-D show the expression of the β-gal is detected in spinal MNs of transgenics staged between E11.0 (FIG. 5B) and E11.5 (FIGS. 5C and D). FIGS. 5E-F show staining was observed at the ventral side of spinal cord in the presence of the evolutionarily conserved 125 bp fragments at E10.5 (FIG. 5E) and E11.5 (FIG. 5F and G), whereas the 313 bp fragments did not have any enhancer activity.

FIGS. 6A-D show the identification of a required element for Hb9 enhancer activity in the spinal cord. FIG. 6A shows two Hox/Pbx binding motifs within 125 bp Hb9 enhancer, and the introduced mutations in construct #6 are indicated. FIG. 6B shows the intact 125 bp Hb9 enhancer drove Hb9 expression in cervical, thoracic, and lumbar levels. FIG. 6C shows in vivo inactivation of the 125 bp Hb9 enhancer by mutations of the two Hox/Pbx binding motifs. Expression in thoracolumbar MNs were not detected, whereas cervical MN expression was not affected. FIG. 6D shows EMSA of HOX and PBX1 binding to a 40 bp wild-type or mutant oligonucleotide derived from 125 bp Hb9 enhancer. Two Hox/Pbx binding motifs are shown in bold. (Top) Two different oligonucleotides, proteins, and antibodies used for binding reactions are indicated. Hox/Pbx indicates the slower migrating complex formed on the wild-type oligonucleotide. FP=free probe. NS=non-specific complexes arising from endogenous ret.

DETAILED DESCRIPTION OF THE INVENTION

One aspect of the present invention relates to an enhancer which functions only in human brain and/or spinal cord motor neurons. The enhancer comprises a nucleotide sequence of SEQ ID NO: 5, SEQ ID NO: 10, or SEQ ID NO: 16 as set forth below.

The enhancer having a nucleotide sequence of SEQ ID NO: 1 is a conserved 438 base pair sequence from the homeobox gene Hb9 which is selectively expressed by motor neurons in the developing central nervous system of human. This nucleotide sequence is as follows:

Human
TGAATAAATTTAAGGGGGCTAATTAATATATAAACTAGCCCAATTTGTCA

AGTTGATTTGTATTTTAGTTAATTGTGAAAGTAATTACCACATGGTCAAA

TTAACAGCTTTCTGGAAATGACCAAGCCTGAGGTTTTATTTCCTTCCTGG

GTGAAGAAAATTCATTTTTCCAAGCTCTTGATGTGATGAATAAAAGTCAT

AAATCTGGGTGATTGGTGCAGGCAGAGTCTAAATGGCTTCATATTTCATT

TTAGGTTTAATAGAAATATTCATGCTCTGTTTTAATGAAATTAAATTGAA

GGGGGATGGGGCCAGAGTGGTTAGCTGATGAATTGACAAAAACTAATCAG

CTTTATTGGGAAACAGGTTAAGGGCACGGGCGTGTCAATAACTCTCAGCC

TGACCCCCTCGTCCATTAGCTCAGGCAGGCTGATTAGA

The corresponding nucleotide sequences for mouse (SEQ ID NO: 2), rat (SEQ ID NO: 3), and Fugu (SEQ ID NO: 4) are as follows:

Mouse
TGAATAAATTTAAGCAGGCTAATTAATATATAAACTAGCTCAATTTGTCA

AGTTGATTTGTATTTTAGTTAATTGTGAAAGTAATTACCACATGGTCAAA

TTAACAGCTTTCTGGAAATGACCAAGCCTGAGGTTTTATTTCCTTCCTGG

GTGAAGAAAATTCATTTTTCCAAGCTCTTGATGTGATGAATAAAAGTCAT

AAATCTGGGTGATTGGTGCAGGCAGAGTCTAAATGGCTTCATATTTCATT

TTAGGTTTAATAGAAATATTCATGCTCTGTTTTAATGAAATTAAATTGAA

GGGGGATGGGCTAGAGTGGTTAGCTGATGAATTGACAAAAACTAATCAG

CTTTATTGGGAAACAGGTTAAGGGCACGACGTGTCAATAACGCTCAGC

CTGACCCCCTCTTCCATTAGCTAGGCAGGCTGATTAGA

Rat
TGAATAAATTTAAGCAGGCTAATTAATATATAAACTAGCCCAATTTGTCA

AGTTGATTTGTATTTTAGTTAATTGTGAAAGTAATTACCACATGGTCAAA

TTAACAGCTTTCTGGAAATGACCAAGCCTGAGGTTTTATTTCCTTCCTGG

GTGAAGAAAATTCATTTTTCCAAGCTCTTGATGTGATGAATAAAAGTCAT

AAATCTGGGTGATTGGTGCAGGCAGAGTCTAAATGGCTTCATATTTCATT

TTAGGTTTAATAGAAATATTCATGCTCTGTTTTAATGAAATTAAATTGAA

GGGGGATGGGCCAGAGTAGTTAGCTGATGAATTGACAAAAACTAATC

AGCTTTATTGGGAAACAGGTTAAGGGCACGGCGTGTCAATAACGCT

CAGCCTGACCCCCTCTTCCATTAGCTAGGCAGGCTGATTAGA

Fugu
TTCATACCTTTTCCGGAAGGTAATTAATATTTAAACTATTTCCGATTTGTC

ACTTTGATTTGTATTTTAGATAATTGTGAATGTAATTACGGAGCAAATTAA

CAGCTTTCAGGAAAGACCGGGTTCTGGGGTCCGGGTCCATCTGAGGCGCCT

TATTAATTTTCTCTCCAATAGCTGTGATGAAAAGGGGCGATAAATCTGGGT

GATCGGTGAAGGCCAATACTAAATGGCTCCATATTTCACCGCTGCTTTAAT

AGAAATATTCATGCGGACACCTTAATGAAATTAAACCGGCGGAAGGCGCA

AGCGCGCTTAGTTGATGAATCGACAAAAACTAATCAGCTTTATTGGTAGAC

AGGTTAAGGGCAACTGGGTGTCAATAATTCTCATTTTGACCTCCTCTTCCA

TTAACTTTAAGTGGCTTATTAGA

An alignment of the human (SEQ ID NO: 1), mouse (SEQ ID NO: 2), and rat (SEQ ID NO: 3) nucleotide sequences yields a conserved sequence of SEQ ID NO: 5 as follows:

TGAATAAATTTAAGXXGGCTAATTAATATATAAACTAGCXCAATTTGTCA

AGTTGATTTGTATTTTAGTTAATTGTGAAAGTAATTACCACATGGTCAAA

TTAACAGCTTTCTGGAAATGACCAAGCCTGAGGTTTTATTTCCTTCCTGG

GTGAAGAAAATTCATTTTTCCAAGCTCTTGATGTGATGAATAAAAGTCAT

AAATCTGGGTGATTGGTGCAGGCAGAGTCTAAATGGCTTCATATTTCATT

TTAGGTTTAATAGAAATATTCATGCTCTGTTTTAATGAAATTAAATTGAA

GGGGGATGGGCXAGAGTXGTTAGCTGATGAATTGACAAAAACTAATCAG

CTTTATTGGGAAACAGGTTX$_{1-0}$AAGGGCACGGACGTGTCAATAACXCTCA

GCCTGACCCCCTCXTCCATTAGCTX$_{0-1}$AGGCAGGCTGATTAGA where X is any nucleotide, where the subscript for X indicates the number of Xs that are present.

The human 438 base pair sequence of SEQ ID NO: 1 consists of non-contiguous 313 base pair and 125 base pair fragments. The 313 base pair human fragment has a nucleotide sequence of SEQ ID NO: 6 as follows:

Human
TGAATAAATTTAAGGGGGCTAATTAATATATAAACTAGCCCAATT

TGTCAAGTTGATTTGTATTTTAGTTAATTGTGAAAGTAATTACCACATGG

TCAAATTAACAGCTTTCTGGAAATGACCAAGCCTGAGGTTTTATTTCCTT

CCTGGGTGAAGAAAATTCATTTTTCCAAGCTCTTGATGTGATGAATAAAA

GTCATAAATCTGGGTGATTGGTGCAGGCAGAGTCTAAATGGCTTCATATT

TCATTTTAGGTTTAATAGAAATATTCATGCTCTGTTTTAATGAAATTAAA

TTGAAGGGGATGGGGCC

The corresponding nucleotide sequences for mouse (SEQ ID NO: 7), rat (SEQ ID NO: 8), and Fugu (SEQ ID NO: 9) are as follows:

Mouse
TGAATAAATTTAAGCAGGCTAATTAATATATAAACTAGCTCAATT

TGTCAAGTTGATTTGTATTTTAGTTAATTGTGAAAGTAATTACCACATGG

TCAAATTAACAGCTTTCTGGAAATGACCAAGCCTGAGGTTTTATTTCCTT

CCTGGGTGAAGAAAATTCATTTTTCCAAGCTCTTGATGTGATGAATAAAA

GTCATAAATCTGGGTGATTGGTGCAGGCAGAGTCTAAATGGCTTCATATT

TCATTTTAGGTTTAATAGAAATATTCATGCTCTGTTTTAATGAAATTAAA

TTGAAGGGGATGGGCT

Rat
TGAATAAATTTAAGCAGGCTAATTAATATATAAACTAGCCCAATT

TGTCAAGTTGATTTGTATTTTAGTTAATTGTGAAAGTAATTACCACATGG

TCAAATTAACAGCTTTCTGGAAATGACCAAGCCTGAGGTTTTATTTCCTT

CCTGGGTGAAGAAAATTCATTTTTCCAAGCTCTTGATGTGATGAATAAAA

-continued
GTCATAAATCTGGGTGATTGGTGCAGGCAGAGTCTAAATGGCTTCATATT

TCATTTTAGGTTTAATAGAAATATTCATGCTCTGTTTTAATGAAATTAAA

TTGAAGGGGATGGGGCC

Fugu
    TTCATACCTTTTCCGGAAGGTAATTAATATTTAAACTATTCCGAT

TTGTCACTTTGATTTGTATTTTAGATAATTGTGAATGTAATTACGGAGCA

AATTAACAGCTTTCAGGAAAGACCGGGTTCTGGGGTCCGGGTCCATCTGA

GGCGCCTTATTAATTTTCTCTCCAATAGCTGTGATGAAAAGGGGCGATAA

ATCTGGGTGATCGGTGAAGGCCAATACTAAATGGCTCCATATTTCACCGC

TGCTTTAATAGAAATATTCATGCGGGACACCTTAATGAAATTAAACCGGC

GGAAGGCGCA

An alignment of the human (SEQ ID NO: 6), mouse (SEQ ID NO: 7), and rat (SEQ ID NO: 8) nucleotide sequence yields a conserved sequence of SEQ ID NO: 10 as follows:

TGAATAAATTTAAGCXGGCTAATTAATATATAAACTAGCXCAATTTGTCA

AGTTGATTTGTATTTTAGTTAATTGTGAAAGTAATTACCACATGGTCAAA

TTAACAGCTTTCTGGAAATGACCAAGCCTGAGGTTTTATTTCCTTCCTGG

GTGAAGAAAATTCATTTTTCCAAGCTCTTGATGTGATGAATAAAAGTCAT

AAATCTGGGTGATTGGTGCAGGCAGAGTCTAAATGGCTTCATATTTCATT

TTAGGTTTAATAGAAATATTCATGCTCTGTTTTAATGAAATTAAATTGAA

GGGGGATGGGGCT where X is any nucleotide.

The human 125 base pair fragment has a nucleotide sequence of SEQ ID NO: 11 as follows:

Human
    AGAGTGGTTAGCTGATGAATTGACAAAAACTAATCAGCTTTATTG

GGAAACAGGTTAAGGGCACGGGCGTGTCAATAACTCTCAGCCTGACCCCC

TCGTCCATTAGCTCAGGCAGGCTGATTAGA

The corresponding nucleotide sequences for mouse (SEQ ID NO: 12), rat (SEQ ID NO: 13), Fugu (SEQ ID NO: 14), and zebrafish (SEQ ID NO: 15) are as follows:

Mouse
    AGAGTGGTTAGCTGATGAATTGACAAAAACTAATCAGCTTTATTG

GGAAACAGGTTTAAGGGCACGGACGTGTCAATAACGCTCAGCCTGACCCC

CTCTTCCATTAGCTAGGCAGGCTGATTAGA

Rat
    AGAGTAGTTAGCTGATGAATTGACAAAAACTAATCAGCTTTATTG

GGAAACAGGTTTAAGGGCACGGGCGTGTCAATAACGCTCAGCCTGACCCC

CTCTTCCATTAGCTAGGCAGGCTGATTAGA

Fugu
    AGCGCGCTTAGTTGATGAATCGACAAAAACTAATCAGCTTTATTG

GTAGACAGGTTAAGGGCAACTGGGTGTCAATAATTCTCATTTTGACCTCC

TCTTCCATTAACTTTAAGTGGCTTATTAGA

-continued
Zebrafish
    AGAGTGGTTAGCTGATGAATTGAGGAAAACTAATCCGCTTTATTG

GTAGACAGGTTAAGGGCAACAGAGTGTCAATAATTCTCTCCCTGACCTCT

TTCTCCATTAGCTTAAAGAGGCTTATAAGA

An alignment of the human (SEQ ID NO: 11), mouse (SEQ ID NO: 13), and rat (SEQ ID NO: 14) nucleotide sequences yields a consensus sequence of SEQ ID NO: 16 as follows:

AGAGTGGTTAGCTGATGAATTGACAAAAACTAATCAGCTTTATTGGGAAA

CAGGTTTAAGGGCACGGXCGTGTCAATAACXCTCAGCCTGACCCCCTCXT

CCATTAGCTX$_{0-1}$AGGCAGGCTGATTAGA where X is any nucleotide, where the subscript for X indicates the number of Xs that are present.

Nucleic acid sequence which are 90%, preferably 95%, similar to the above sequences are encompassed by the present invention.

Another embodiment of the present invention relates to an isolated nucleic acid construct which includes an enhancer which functions only in human brain and/or spinal cord motor neurons. The enhancer comprises a nucleotide sequence of SEQ ID NO: 5, SEQ ID NO: 10, or SEQ ID NO: 16. The construct also has a nucleic acid encoding a marker protein and a 3' control region, where the enhancer, the nucleic acid encoding a marker protein, and the 3' control region are positioned with respect to one another to permit expression of the marker protein.

Another aspect of the present invention relates to a method of isolating an enriched or purified population of motor neurons from a mixed population of human brain and/or spinal cells. This involves providing a mixed population of human brain and/or spinal cord cells comprising motor neurons and providing an enhancer which functions only in motor neurons, where the enhancer comprises a nucleotide sequence of SEQ ID NO: 5, SEQ ID NO: 10, or SEQ ID NO: 16. The nucleic acid molecule encoding a marker protein under control of the enhancer is introduced into the mixed population of human brain and/or spinal cord cells comprising motor neurons. Only the motor neurons are allowed to express the marker protein. The cells expressing the marker protein are separated from the mixed population of human brain and/or spinal cord cells comprising motor neurons. As a result, an enriched or purified population of motor neurons is isolated.

A mixed population of human brain and/or spinal cord cells can be provided by providing a population of human embryonic stem cells and inducing the population of human embryonic stem cells to produce the mixed population of human brain and/or spinal cord cells comprising motor neurons. The inducing step can take place before or after introducing the enhancer into the mixed population of human brain and/or spinal cord cells (preferably embryonic stem cells). The inducing is carried out by administering an inducer, such as retinoic acid, sonic hedgehog, or mixtures thereof.

The marker protein is preferably a green fluorescent protein. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (U.S. Pat. No. 5,491,084 to Chalfie et al., which are hereby incorporated in their entirety). A plasmid designated pGFP10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 75547 on Sep. 1, 1993. This plasmid is commercially available from the ATCC and comprises a cDNA which encodes a green fluorescent protein of *Aequorea victoria* as disclosed in U.S. Pat. No. 5,491,084 to Chalfie et al., which is hereby incorporated in its entirety. A mutated form of this GFP (a red-shifted mutant form) designated pRSGFP-C1 is commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. Alternatively, the GFP can be in humanized form (GFPh) (Levy, J., et al., *Nature Biotechnol.* 14:610-614 (1996), which is hereby incorporated in its entirety). Any nucleic acid molecule encoding a fluorescent form of GFP can be used in accordance with the subject invention.

Other suitable marker proteins include lacZ/beta-galactosidase or alkaline phosphatase.

Standard techniques are then used to place the nucleic acid molecule encoding marker protein-encoding nucleic acid molecule under the control of the chosen cell specific promoter. Generally, this involves the use of restriction enzymes and ligation.

The resulting construct, which comprises the nucleic acid molecule encoding the marker protein under the control of the selected enhancer (themselves a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses, *lentivirus, adenovirus, herpesvirus*, and adeno-associated virus.

As indicated, some of these methods of transforming a cell require the use of an intermediate plasmid vector. U.S. Pat. No. 4,237,224 to Cohen and Boyer, which is hereby incorporated in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al., *Molecular Cloning: A Laboratory Manual*, 2d Edition, Cold Spring Harbor Laboratory Press, Cold Spring Harbor, N.Y. (1989), which is hereby incorporated in its entirety.

In accordance with one of the above-described methods, the nucleic acid molecule encoding the GFP is thus introduced into a plurality of cells. The enhancer which controls expression of the GFP, however, only functions in the cell of interest. Therefore, the GFP is only expressed in the cell of interest. Since GFP is a fluorescent protein, the cells of interest can, therefore, be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N. Mex.). They can be separated in bulk through fluorescence activated cell sorting, a method that effectively separates the fluorescent cells from the non-fluorescent cells.

By carrying out the method of the present invention, a variety of motor neurons can be obtained, including spinal motor neurons, brain stem motor neurons, cranial motor neurons, and visceral motor neurons. These motor neurons (as well as the mixed population of motor neurons) can be of fetal, postnatal, and adult origin.

Once the enriched or purified population of motor neurons is isolated in accordance with the present invention, those neurons can be transplanted into a subject. Such transplantation is expected to be beneficial in treating subjects with: amyotrophic lateral sclerosis; spinal muscular atrophies; poliovirus and West Nile virus-induced motor neuronopathy; brachial and lumbosacral plexus root avulsions; traumatic, infectious and radiation-induced spinal nerve root injuries; and myeloradiculitis.

Another aspect of the present invention relates to an isolated nucleic acid construct which includes an enhancer which functions only in human brain and/or spinal cord motor neurons, a basal promoter, a nucleic acid encoding a therapeutic protein, and a 3' control region. The enhancer comprises a nucleotide sequence selected from the group consisting of SEQ ID NO: 5, SEQ ID NO: 10, and SEQ ID NO: 16. The enhancer, the basal promoter, the nucleic acid encoding a therapeutic protein, and the 3' control region are positioned with respect to one another to permit expression of the therapeutic protein.

The therapeutic protein can be BDNF, NT-3, NT-4, erythropoietin, VEGF, IGF1, neuroregulin, or CTNF.

This nucleic acid construct containing a nucleic acid molecule encoding a therapeutic protein can be incorporated into a viral vector. The viral vector can be an adenoviral vector, an adeno-associated viral vector, a lentiviral vector, or a herpesviral vector.

This viral vector can be used in carrying out a method of therapeutically targeting motor neurons. In particular, this method involves administering the viral vector under conditions effective to infect motors neurons. As a result, the motor neurons are therapeutically targeted.

Within the viral vector is the therapeutic protein which can be BDNF, NT-3, NT-4, erythropoietin, VEGF, IGF1, neuroregulin, or CTNF.

This method can be carried out in vitro or in vivo. The method can be used to treat a subject for a variety of conditions, including: a disease of motor neurons (e.g., amyotrophic lateral sclerosis or the spinal muscular atrophies), an infectious or inflammatory disease of spinal cord motor neurons (e.g., flaviviral encephalomyelitis, West Nile virus, *poliovirus, enterovirus*, HTLV3, or *cytomegalovirus*), spinal cord injury or spinal root trauma, epidural compression and destruction of the spinal nerve roots, or myeloradiculopathy. This therapy is carried out by injection of the virus encoding the motor neuron-targeted therapeutic transgene into either the spinal cord, cerebrospinal fluid, or muscle targets of the affected motor neurons, the latter allowing infection of motor neuron fibers in the musculature with transport of the transgene back to the motor neuron cell body, and protein synthesis therein. Depending upon the disease target, the virus may also be injected systemically via intravenous or intra-arterial infusion. By such means, viral infection would be widespread, but transgene expression would nonetheless be limited to motor neurons because of the specificity of the enhancer.

EXAMPLES

Example 1

Homology Screening

A 9 kb 5' non-coding fragment of the mouse Hb9 gene was sequenced. The corresponding human genome sequence was obtained form Ensembl genome browser (www.ensemble.org). Blast 2 sequences program (www.ncbi.nih.gov/blast/b12seq/b12.html) was used to identify conserved non-coding regions of the Hb9 gene between mouse and human. Ensembl genome browser was also used to identify evolutionarily conserved non-coding sequences of the Hb9 genes among mouse, rat, human, pufferfish, and zebrafish, and then multiple sequence alignments were conducted using MacVector (Accelrys).

Example 2

Transgenic Construct

Construct #1 (3.6 kb Hb9 enhancer-β-globin-lacZ) was generated by inserting a 3.6 kb NotI/Sse8387I fragment derived from a 9 kb 5' non-coding fragment of the mouse Hb9 gene into the NotI/PstI sites of the reporter construct BGZA, which contains the β-globin minimal promoter, lacZ gne, and SV40 polyadenylation cassette. Construct #2 (5.4 kb Hb9 promoter-lacZ) contains a 5.4 kb Sse8387I/PmeI fragment of the 9 kb Hb9 promoter region into the PstI/SmaI sites of placZpA. Construct #3 (438 bp Hb9 enhancer-β-globin-lacZ) was obtained by cloning 313 bp and 125 bp fragment derived from Construct #4 and #5, respectively, to BGZA.

Construct #4 (313 bp Hb9 enhancer-β-globin-lacZ): A 313 bp fragment was PCR amplified with the primers:

```
                                        (SEQ ID NO: 17)
5'-ATAGCATAGCGGCCGCTGAATAAATTTAAGCAGGCT-3', (SEQ ID NO: 18)
5'-GCTCTAGAAGCCCCATCCCCCTTCAAT-3',
and cloned into BGZA.
```

Construct #5 (125 bp Hb9 enhancer-β-globin-lacZ): A 125 bp fragment was PCR amplified with the primers:

```
                                        (SEQ ID NO: 19)
5'-GACTAGTAGAGTGGTTAGCTGATGAAT-3', (SEQ ID NO: 20)
5'-TCACCCGGGTCTAATCAGCCTGCCTAGCT-3',
``` and cloned into BGZA. Construct #4 and #5 contain three copies of the 313 bp and 125 bp fragments, respectively, in order to drive the reporter gene expression more efficiently.

Construct #6: The site-directed mutagenesis construct was generated according to the Ho's method (Ho et al., *Gene* 77:51-9 (1989), which is hereby incorporated by reference in its entirety) using the primers:

```
                                        (SEQ ID NO: 21)
5'-ATAGCATAGCGGCCGCTGAATAAATTTAAGCAGGCT-3'

(SEQ ID NO: 22)
5'-TCGTTCGTTTTTGTCAACGCACGAGCTAACCACTCTGGCTGGA-3', (SEQ ID NO: 23)
5'-TCGTGCGTTGACAAAAACGAACGAGCTTTATTGGGAAACAGGT-3'.

(SEQ ID NO: 24)
5'-TCACCCGGGTCTAATCAGCCTGCCTAGCT-3'
```

All PCR-amplified fragments were verified by sequencing.

Example 3

Production and Genotyping of Transgenic Mice

Transgenes for injection were separated from vector sequences using 1% Seakim LE agarose (BMA), purified on QIAquick gel extraction kit (Qiagen), precipitated in injection buffer. Transgenic mice were generated by standard procedures (Hogan et al., *Cold Spring Harbor Laboratory Press, Cold Spring Harbor* (1994), which is hereby incorporated by reference in its entirety) using fertilized eggs from B6D2F1 9C57BL/6xDBA) crosses. Transgenics were identified by PCR with the lacZ primers 5'-CGAGTGTGATCATCTG-GTCG-3' (SEQ ID NO: 25) and 5'-TTACCTTGTGGAGC-GACATC-3' (SEQ ID NO: 26) using genomic DNA extracted from yolk sacs or tails.

Example 4 lacZ Detection

β-Gal Staining of whole-mount embryos Staged embryos were dissected from the uterus in cold PBS and fixed for 45 min at 4C in fixing solution (1% formaldehyde, 0.2% glutaraldehyde, 0.02% NP-40 in PBS pH 7.4). Whole-mount β-gal staining was performed as described (Ovitt et al., Microinjection and Transgenesis, 427-37 (1997), which is hereby incorporated by reference in its entirety).

β-Gal Staining of Spinal Cord tissue To examine β-gal Staining in adult spinal cord, stable transgenic lines carrying Construct #1 (3.6 kb Hb9 enhancer-β-globin-lacZ) were established. Genotyped adult transgenic mice were killed and perfusion fixed (1% formaldehyde, 0.2% glutaraldehyde, 0.02% NP-40 in PBS pH 7.4), and their spinal cords removed. After β-gal staining (Ovitt et al., *Microinjection and Transgenesis*, 427-37 (1997), which is hereby incorporated by reference in its entirety), post-fixation was performed in the same fixative for 1-2 hr at 4C.

Example 5

Immunohistochemistry

Embryos or adult spinal cords were cryosectioned at 15 μm, permeabilized with PBS, 0.1% saponin and 1% NGS, and blocked with PBS, 0.05% saponin and 5% NGS, each for 30 min. Sections were labeled with mouse anti-Islet1 (39.4D5, 1:100, DSHB), mouse anti-MNR2/Hb9 (5C10, 1:3, DSHB) or anti-ChAT (1:1000, Chemicon) overnight at 4° C. Species- and isotype-specific biotin-labeled secondary antibodies were applied at 1:100 for 2 h at room temperature. Staining was performed using the ABC kit (Vector) and DAB peroxidase substrate (Sigma, D-4293).

Example 6

Protein Production and EMSA (Electophoretic Mobility Shift Assay)

PBX1 and HOX proteins used in this study were produced in vitro from the corresponding pSG5-derived expression vectors using a T7 polymerase-based coupled transcription-translation reticulocyte lysate system (Promega, Madison, Wis.). EMSA were performed according to the instruction of DIG gel shift kit (Roche). Briefly, 2 μl of double-stranded DIG-labeled oligonucleotides were incubated with 2 μl of in vitro-translated proteins in 20 μl of binding buffer (20 mM Hepes pH 7.6, 1 mM EDTA, 10 mM $(NH_4)_2SO_4$, 1 mM DTT, 0.2%(w/v) Tween 20, 30 mM KCl in the presence of 1 μg of poly (dI-dC) and 0.1 μg of poly L-lysine) for 30 min at room temperature. Pre-binding reactions of unlabeled competitor oligonucleotides at ~100-fold molar excess occurred for 15 minutes at room temperature. The incubation mixture was resolved by electrophoresis and served for chemiluminescent detection according to recommended conditions of DIG gel shift kit (Roche). DIG-labeled DNA probes used were generated by annealing complementary oligonucleotides:

```
Wild-type oligonucleotide probe (40 bp)
                                         (SEQ ID NO: 27)
5'-GTACGTTAGCTGATGAATTGACAAAAACTAATCAGCTTTA-3'

Mutant oligonucleotide probe (40 bp)
                                         (SEQ ID NO: 28)
5'-GTACGTTAGCTCGTGCGTTGACAAAAACGAACGAGCTTTA-3'
```

Example 7

Identification of a 3.6 kb MN Enhancer Within the Hb9 Gene

Previous work identified a 9 kb 5' fragment of the mouse Hb9 gene which is sufficient to direct spinal MN expression in vivo (Arber et al., *Neuron* 23:659-74 (1999), Wichterle et al., *Cell* 110:385-397 (2002), which are hereby incorporated by reference in their entirety). To define the cis-acting regulatory sequences that govern the expression of Hb9 by MNs, conserved regions between mouse and human Hb9 genomic sequences were first identified. Such conservation across species of noncoding sequences in the vicinity of a gene frequently marks the presence of regulatory elements (Muller et al., *Bioessays* 24:564-72 (2002), which is hereby incorporated by reference in its entirety). The genomic sequences of mouse and human 9 kb Hb9 promoter were thus compared. Five clusters of remarkably high nucleotide sequence conservation (81% to 94%) were found (FIG. 1A; conserved regions less than 70 bp are not shown). Three of them were located within a 5' 3.6 kb fragment, whereas the other two were within the 5.4 kb Hb9 promoter region.

To identify which of these elements directed Hb9 expression, two transgenes were established, each of which was placed in control of lacZ (FIG. 1B). Transgene #1 containing the 3.6 kb Hb9 fragment was tested for enhancer activity by placing it 5' of the β-globin basal promoter (P/β-globin) in a lacZ reporter vector, BGZA. This vector contains lacZ placed under control of human P/β-globin, with an SV40 polyadenylation cassette; in transgenics, it is inactive in the absence of an enhancer (Yee et al., *Genes Dev* 7:1277-89 (1993), Helms et al., *Development* 127:1185-96 (2000), which are hereby incorporated by reference in their entirety). The resultant plasmid was designated E/Hb9 (3.6 kb):lacZ. For transgene #2, the 5.4 kb Hb9 promoter was used intact, directly driving lacZ with a polyA cassette, yielding the plasmid P/Hb9 (5.4 kb):lacZ.

Using these constructs, gene expression patterns were identified in transgenic embryos at 10.0-11.5 dpc. P/Hb9 (5.4 kb):lacZ (transgene #2) did not activate lacZ expression in the neural tube (FIG. 1D). In contrast, E/Hb9(3.6 kb):lacZ (transgene #1) exhibited activity similar to that of transgenic embryos with the entire 9 kb Hb9 promoter at E10.5-11.5 (FIGS. 1C, 2A-C) (Arber et al., *Neuron* 23:659-74 (1999), which is hereby incorporated by reference in its entirety). These results were consistent in at least 4 embryos bearing each transgene. In the E/Hb9 (3.6 kb) mice, lacZ expression was noted in the ventral spinal cord at virtually all cervical, thoracic, and lumbar levels. Transverse sections revealed lacZ in the ventral horns and axons extending from the areas (FIG. 2D), suggesting the motor neuron specificity of E/Hb9 (3.6 kb) at E10.5-11.5. These lacZ$^+$ cells co-expressed the MN transcription factors, Islet-1 (FIG. 2E), and Hb9. Together, these results indicated that the 3.6 kb fragment of Hb9 acts as a MN-specific enhancer. At E11.5 β-gal was noted within the trigeminal and facial motor nuclei as well as olfactory epithelium (FIGS. 1D, 2A-C), where endogenous HB9 protein is not expressed (Thaler et al., *Neuron* 23:675-87 (1999), which is hereby incorporated by reference in its entirety).

The establishment of stable transgenic lines of E/Hb9 (3.6 kb):lacZ mice allowed examination of gene expression in adult spinal cord as well. Several litters from each of two independent transgenic lines were analyzed 8-12 weeks after birth. As in embryos, E/Hb9-driven lacZ was restricted to magnocellular neurons that reside in the median and lateral motor columns of the ventral spinal cord (FIGS. 3A, C). lacZ$^+$ cells extended axons from ventral horns (FIG. 3B) and co-expressed ChAT (FIG. 3D), suggesting that they are MNs. No differences were seen between two lines. Thus, the 3.6 kb Hb9 enhancer continues to direct MN-specific gene expression in the adult spinal cord.

Example 8

The 3.6 kb Hb9 Enhancer Harbors Evolutionarily Conserved 313 bp and 125 bp Fragments To identify cis-acting elements that might directly regulate MN specification, cross-species homology screening was next used to identify conserved elements within the 3.6 kb Hb9 enhancer. Comparison of mouse, rat, human, and pufferfish (*Fugu rubripes*) 3.6 kb genomic sequences revealed two blocks of high homology, of 313 bp (region A) and 125 bp (region B) (FIG. 4A). It was found that both regions A and B were located within the 5' regulatory region of the Hb9 genes, confirmed by perfect conservation of the homeobox regions in these species (FIG. 4B). Overall, regions A and B exhibited 74% and 82% homology between mouse and Fugu, respectively (FIGS. 4C-E). In Fugu, these two conserved regions were located within the first 2 kb upstream of the Hb9 coding region; in contrast, their corresponding sequences in mouse and human were about 8 kb 5' of the Hb9 translation start site (FIG. 4A). This is consistent with Fugu's relatively compact genome. At approximately 400 mb, it is nine times smaller than the mouse or human genome, even though each of these genomes has a similar number of genes (Brenner et al., *Nature* 366:265-8 (1993), Aparicio et al., *Science* 297:1301-10 (2002), which are hereby incorporated by reference in their entirety).

The Hb9 genomic sequence in the zebrafish (*Danio rerio*) was also analyzed, and two copies of the identical region B sequence were found within 2 kb of the Hb9 translation start (FIG. 3A). In contrast to Fugu, no region A sequence was found in the zebrafish Hb9 locus, or for that matter anywhere else in the whole zebrafish genome, suggesting the region B might play a more important role than region A in Hb9 gene expression.

Example 9

125 bp Hb9 Enhancer was Sufficient to Direct MN-specific Gene Expression in Transgenic Mice For functional analysis of the two conserved sequences A and B, several constructs were generated whose relative abilities to drive MN-specific reporter gene expression were assessed in transgenics. Construct #3 was constructed to include both putative enhancers A and B. It is a 438 bp synthetic chimera that consists of the otherwise noncontiguous 313 bp and 125 bp fragments (FIG. 5A). Transgenic analysis showed that this 438 bp sequence was capable of appropriate temporal and spatial activation of a reporter gene in the ventral spinal cords (FIGS. 5B-D). Other than slight lacZ expression in the facial nerve, no other ectopic gene expression was noted with this construct at E10.5-11.5. This result indicated that the Hb9 regulatory regions contained within the 438 bp chimera of enhancers A and B are sufficient to specify MN gene expression.

Next, construct #4 and #5 were generated, which contained three copies of either the 313 bp (fragment A) or 125 bp (fragment B) regions, respectively (FIG. 5A), to investigate whether either of these fragments was alone sufficient to direct MN-specific β-gal expression. Construct #4 expressed no β-gal at E10.5-11.5. In contrast, construct #5 expressed β-gal in the ventral spinal cord, similar to the expression pattern of constructs #1 and #3 at E10.5-11.5 (FIGS. 5E-G). However, ectopic expression of construct #5 was seen in several regions, including the ventral midbrain. Taken together, these results demonstrate that the 125 bp element was sufficient to direct MN-specific gene expression. As such, fragment B constitutes the Hb9 core enhancer.

Example 10

The Requirement of Hox/Pbx Sites for the 125 bp Hb9 Enhancer Activity

To identify potential transcription factor binding sites within 125 bp Hb9 enhancer that might suggest upstream factors important for Hb9 expression in MNs, MATInspector (Quandt et al., *Nucleic Acids Res* 23:4878-84 (1995), which is hereby incorporated by reference in its entirety) was used to search TRANSFAC database (Heinemeyer et al., *Nucleic Acids Res* 26:362-7 (1998), which is hereby incorporated by reference in its entirety). This revealed two sequences (boxed in FIG. 5A) highly related to a bipartite Hox/Pbx (HP) consensus binding sequence (TGATNNAT) (Chan et al., *Proc Natl Acad Sci USA* 93: 5223-8 (1996), which is hereby incorporated by reference in its entirety) within 125 bp sequence. These two binding sequences were well conserved among mouse, human, rat, pufferfish, and zebrafish (FIG. 5B). There is emerging evidence that HOX proteins are expressed in MNs (Tiret et al., *Development* 125:279-91 (1998), Liu et al., *Neuron* 32:997-1012 (2001), which are hereby incorporated by reference in their entirety), and the HOX proteins have been implicated as critical determinants of spinal MN identity and organization (Dasen et al., *Nature* 425:926-33 (2003), which is hereby incorporated by reference in its entirety). Therefore, it seemed likely that the two conserved bipartite HP motifs within 125 bp Hb9 enhancer were involved in the transactivation of the Hb9 gene.

To test this hypothesis, construct #6 was generated by introducing mutations in two HP sites, converting them from TGATNNAT to TCGTNCGT (FIG. 6A). It was confirmed that HOX/PBX proteins failed to form protein-DNA complexes with these mutated HP motifs (FIG. 6D), as previously reported (Maconochie et al., *Genes Dev* 11:1885-95 (1997), which is hereby incorporated by reference in its entirety). Mutations of these sequences did not affect cervical Hb9 gene expression, but completely disrupted more posterior MN-specific gene expression. (FIGS. 6B-C). Thus, the HP motifs within 125 bp Hb9 enhancer play a critical role in directing MN-specific gene expression in vivo.

Example 11

Cooperative Binding of HOXB and PBX1 Proteins on HP Sites

Next, a representative subset of HOX proteins was tested for cooperative DNA binding with Pbx 1, to both the wild-type and a mutated 40 bp sequence derived from the 125 bp Hb9 enhancer (FIG. 6D). In the presence of PBX1, only HOXB1 and HOXB3 proteins (FIG. 6D, lanes 2 and 3) formed a detectable retarded complex with a DIG-labeled wild-type oligonucleotide. No binding was detected with PBX1 alone (lane 1), or with either of the HOX proteins alone. Polyclonal antibodies against full-length PBX1 protein completely abolished the formation of the HoxB1-Pbx1 complex (lane 6). In addition, the introduction of seven point mutations in the core HP motifs abolished cooperative Hox-Pbx complex formation (lane 8-11). Similarly, Di Rocco et al. reported that HOX paralog group 2 (HoxB genes), but not 3 (HoxC) or 4 (HoxD), can form a complex with b 1-ARE (the 148 bp autoregulatory element driving HoxB1 expression), in the presence of PBX1 (Di Rocco et al., *Embo J* 16:3644-54 (1997), which is hereby incorporated by reference in its entirety).

Example 12

Evolutionary Conservation of Hb9 Regulatory Elements

Homology searches between genomic sequences of evolutionary distant species offer a fast detection method for gene regulatory sequences (Muller et al., *Bioessays* 24:564-72 (2002), which is hereby incorporated by reference in its entirety), and the contracted genomes of the pufferfish and zebrafish have successfully been used to identify conserved regulatory elements in vertebrates (Aparicio et al., *Proc Natl Acad Sci USA* 92:1684-8 (1995), which is hereby incorporated by reference in its entirety). Using this technique, a 3.6 kb fragment, and then two evolutionarily conserved elements that consist of noncontiguous 313 bp (region A) and 125 bp (region B) fragments within the 9 kb mouse Hb9 promoter were identified. Transgenic analysis showed that when two fragments, namely 313 bp and 125 bp, were put together, the resultant 438 bp sequence was capable of appropriate temporal and spatial activation of a reporter gene in spinal MNs. β-gal expression under this enhancer appeared to largely coincide with endogenous Hb9 expression, but there were a few discrepancies. They are 1) the lack of expression in the most caudal region of spinal cord in transgenic animals and 2) ectopic β-gal expression in facial nerve in transgenics. No endogenous Hb9 expression was found in facial nerves (Thaler et al., *Neuron* 23:675-87 (1999), which is hereby incorporated by reference in its entirety). Given the difficulty of detecting small fragments of evolutionarily conserved sequences (especially less than 80 bp) by blast search, it is possible that there are other functional sequences—both enhancers and silencers—within the 9 kb Hb9 promoter. Nonetheless, the above results showed that the identified 125 bp covered most of spinal MNs.

Next, further sequence conservation analysis was conducted using the zebrafish genomic sequence. Interestingly, the zebrafish genome does not contain sequences that are homologous to the 313 bp region A; instead, blast search detected two copies of the identical region B sequences, namely B1 and B2 regions. Transgenic analysis showed that the 125 bp region B was necessary and sufficient for MN-specific expression in vivo. Thus, the 125 bp represents the MN-specific Hb9 core enhancer.

Recently, Lee et al. separately identified a 250 bp MN enhancer (Lee et al., *Neuron* 38:731-745 (2003), Lee et al., *Development* 131:3295-3306 (2004), which are hereby incorporated by reference in their entirety) based on the high genomic sequence conservation between human and mouse (>90%). This sequence does not overlap with the evolutionarily conserved 125 bp or 438 (313+125) bp fragment that was identified here. Rather, the 250 bp MN enhancer is not conserved across phylogeny; extensive blast searches failed to identify highly homologous sequences in either the Fugu or zebrafish Hb9 genomic loci. In contrast, the percentage identity of the 125 bp Hb9 enhancer sequences among evolutionarily distinct species, including Fugu and zebrafish, exceeded 82%. One explanation for why many enhancer regions are so highly conserved is that they contain binding sites for multiple upstream transcription factors (TFs), whose concurrent presence is required for enhancer activity. This would result in a high level of potential regulatory control of gene expression. However, in Hb9, it cannot be ruled out that there are two distinct MN enhancers (the present 125 bp fragment and Lee's 250 bp fragment), and that each alone might be sufficient to drive MN-specific gene expression.

Previous work identified 4.4 kb Ngn2 enhancer that showed similar pattern of spinal gene expression pattern with 125 bp Hb9 enhancer (Simmons et al., *Dev Biol* 229:327-39 (2001), which is hereby incorporated by reference in its entirety). However, a blast search between Hb9 and Ngn2 enhancers detected no significant similar sequences, suggesting that the respective expression of these genes is regulated by different upstream transcription factors. Moreover, a blast search was conducted to identify other MN-specific genes (e.g. Islet1, ChAT) that share considerable homology with the Hb9 125 bp enhancer, but no such blast hit was detected, indicating this enhancer may be regulated uniquely. Unlike 125 bp region B, the 313 bp region A had no enhancer activity. Consistent with this, the zebrafish genome lacks homology to the 313 bp region A. The role of 313 bp sequence is not clear, but it might function as a silencer that suppresses gene expression other than MNs. Consistent with this idea, the above results showed that without 313 bp sequence, resulting 125 bp conferred more ectopic β-gal expressions.

Example 13

MN-specific Gene Expression by 3.6 kb Hb9 Enhancer

Both Hb9 and Islet-1 are expressed in adult, as well as developing, MNs (Vult von Steyern et al., *Eur J Neurosci* 11:2093-102 (1999), which is hereby incorporated by reference in its entirety). It was tested whether the identified Hb9 enhancer is capable of driving Hb9 expression in adult as well as developing MNs. The 3.6 kb Hb9 enhancer was used, because it confers strong β-gal expression in MNs more so than that afforded by the 438 bp enhancer. Thus, 3.6 kb Hb9 enhancer can target not only newly generated MNs but also adult MNs. This enhancer may prove useful in establishing MN-targeted gene therapy vectors as a means of specifically delivering therapeutic transgenes to vulnerable cells in the motor neuron diseases such as spinal muscular atrophy and amyotrophic lateral sclerosis. For example, because *lentivirus* vectors have the approximately 8 kb cloning capacity, the identified 3.6 kb enhancer may be useful to selectively over-express any gene of interest (e.g. GDNF, erythropoietin, and/ or Bcl-2) to prevent MN cell death. Alternatively, 3.6 kb Hb9 enhancer itself can be used as a MN selection vector, for instance via fluorescence-activated cell sorting (FACS), based on enhancer-specified GFP expression (Roy et al., *Nature Biotechnology* 22:297-305 (2004), which is hereby incorporated by reference in its entirety).

Example 14

A Role of Hox/Pbx Binding Sequences in Regulating Hb9 Expression

Lee and Pfaff reported that Ngn2/NeuroM transcriptionally synergize with Islet-1 and Lhx3 to directly bind the 250 bp Hb9 enhancer, thereby activating Hb9 expression (Lee et al., *Neuron* 38:731-745 (2003), which is hereby incorporated by reference in its entirety). However, most reported regulators of Hb9 expression, such as Nkx6.1 and Olig2, are transcriptional repressors that do not appear to directly drive Hb9 expression. Accordingly, the conserved 125 bp Hb9 enhancer does not contain E-box sites, suggesting that it may not be regulated by Ngn2/NeuroM. Rather, it was posited that the 125 bp Hb9 enhancer might direct MN-specific gene expression following binding by other transcription factors, yet-to-be identified.

To better elucidate these alternative molecular pathway of MN induction, TF binding site analysis of the 125 bp Hb9 enhancer was first performed. This revealed two potential Hox/Pbx (HP) binding sequences (FIG. 4E), within the 125 bp Hb9 enhancer, that were also evolutionarily conserved. Along the A-P axis, the overlapping, or nested, expression pattern of HOX HD proteins provides positional values that influence the fate of neurons (Lumsden et al., *Science* 274: 1109-15 (1996), which is hereby incorporated by reference in its entirety), and there is emerging evidence that HOX proteins are expressed in MNs (Tiret et al., *Development* 125: 279-91 (1998), Liu et al., *Neuron* 32:997-1012 (2001), which are hereby incorporated by reference in their entirety). Moreover, in the developing hindbrain, misexpression of Hoxa2 or Hoxb1 leads to the generation ectopic MNs in this territory, even though it is normally devoid of this cell type (Jungbluth et al., *Development* 126:2751-8 (1999), which is hereby incorporated by reference in its entirety). The present mutagenesis study showed that HP binding sites were essential for Hb9 expression in thoracolumbar MNs, but not for the cervical region, suggesting HP could be one of critical upstream regulators of the Hb9 gene. Consistent with this explanation, HOXB 1 and HOXB3 bound to the wild-type sequence derived from the 125 bp Hb9 enhancer in the presence of PBX1 in vitro whereas HOXC8 or HOXD9 did not form the retarded complex. None of HOX proteins binded to the mutated oligonucleotide with PBX1. The present results suggested that HoxB genes are likely to play an important role in regulating Hb9 expression. It is noteworthy that HoxB genes, but not HoxC or HoxD genes, were shown previously to bind b1-ARE in vitro, and regulate HoxB1 expression (Di Rocco et al., *Embo J* 16:3644-54 (1997), which is hereby incorporated by reference in its entirety). It is also worth noting that one of two HP binding sequences contains an overlapping binding sequence of bicoid-class homeoprotein (TAATC). However, since none of the known bicoid-class homeoproteins including Otx, Goosecoid (Gsc), and Pitx, are expressed in the developing spinal cord (Gaunt et al., *Development* 117:769-78 (1993), Simeone et al., *Embo J* 12:2735-47 (1993), Gage et al., *Mamm Genome* 10:197-200 (1999), which are hereby incorporated by reference in their entirety), bicoid binding would appear unimportant to MN gene expression.

Taken together, these results suggest that the evolutionarily conserved 125 bp region B is a MN-specific Hb9 core enhancer; as such, the molecular pathways regulating Hb9 expression would appear to be evolutionarily conserved. Moreover, these results point out that comparing the genomic sequence of mammalian regulatory regions with those of lower vertebrates, in this case pufferfish and zebrafish, can greatly facilitate studies of eukaryotic transcriptional regulation. These data also suggest that HOX/PBX proteins are necessary for the expression of Hb9 to thoracolumbar MNs, and as such, play a critical role in the segmental specification of spinal MNs. It is likely that cervical Hb9 expression is regulated by other unidentified TFs. Thus, dorsoventral patterning of the spinal cord, and Shh-dependent MN specification in particular, would appear to be coordinated with the rostrocaudal patterning of MNs through HOX/PBX proteins. Besides the developmental insights brought to bear by the identification and analysis of the Hb9 core enhancer, this sequence may have great practical and translational value: MN-specifying elements such as the Hb9 core enhancers may permit creation of not only MN-specific selection vectors, as noted (Roy et al., *Nature Biotechnology* 22:297-305 (2004), which is hereby incorporated by reference in its entirety), but also MN-targeted plasmid and viral vectors for gene therapy. These in turn may permit systemic and whole CNS administration of gene therapeutics, that may be effectively and specifically targeted to the spinal MNs using the Hb9 enhancer.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of expressing a transcript of interest specifically in motor neurons of a subject, said method comprising:
   providing a viral vector comprising a nucleic acid construct comprising:
   an enhancer which functions in human brain motor neurons or spinal cord motor neurons, wherein the enhancer comprises a nucleotide sequence of SEQ ID NO: 5; a basal promoter; a nucleic acid encoding the transcript of interest; and a 3' control region, wherein the enhancer, the basal promoter, the nucleic acid encoding the transcript of interest, and the 3' control region are operably linked for expression of the transcript of interest and
   administering the viral vector directly to the subject's spinal cord or brain that comprise the motor neurons, or to a muscle innervated by the motor neurons wherein the vector is delivered to the motor neurons of the subject and the transcript of interest is expressed therein.

2. The method of claim 1, wherein the transcript of interest encodes a protein selected from the group consisting of BDNF, NT-3, NT-4, erythropoietin, VEGF, IGF1, neuregulin, and CTNF.

3. The method of claim 1, wherein the viral vector is selected from the group consisting of an adenoviral vector, an adeno-associated viral vector, a lentiviral vector, and a herpes viral vector.

4. The method of claim 1, wherein the nucleotide sequence of SEQ ID NO: 5 comprises a sequence selected from the group consisting of SEQ ID NO: 1, SEQ ID NO: 2, and SEQ ID NO: 3.

5. The method of claim 4, wherein the nucleotide sequence of SEQ ID NO: 5 comprises the nucleotide sequence of SEQ ID NO: 1.

6. An enhancer which functions in human brain or spinal cord motor neurons, wherein the enhancer comprises the nucleotide sequence of SEQ ID NO: 5.

7. The enhancer of claim 6 wherein the nucleotide sequence of SEQ ID NO: 5 comprises the nucleotide sequence of SEQ ID NO: 1.

8. The enhancer of claim 6 wherein the nucleotide sequence of SEQ ID NO: 5 comprises the nucleotide sequence of SEQ ID NO: 2.

9. The enhancer of claim 6 wherein the nucleotide sequence of SEQ ID NO: 5 comprises the nucleotide sequence of SEQ ID NO: 3.

10. An isolated nucleic acid construct comprising:
    an enhancer which functions in a motor neuron selected from at least one of a human brain motor neuron and a spinal cord motor neuron, wherein the enhancer comprises a nucleotide sequence selected from the group consisting of SEQ ID NO: 5 and SEQ ID NO: 16;
    a nucleic acid encoding a marker protein; and
    a 3' control region, wherein the enhancer, the nucleic acid encoding the marker protein, and the 3' control region are operably linked for expression of the marker protein.

11. The isolated nucleic acid construct of claim 10, wherein the nucleotide sequence of SEQ ID NO: 5 comprises a nucleotide sequence of SEQ ID NO: 1.

12. The isolated nucleic acid construct of claim 10, wherein the nucleotide sequence of SEQ ID NO: 5 comprises a nucleotide sequence of SEQ ID NO: 11.

13. The isolated nucleic acid construct of claim 10, wherein the marker protein is a fluorescent protein.

14. The isolated nucleic acid construct of claim 10, wherein the marker protein is either beta-galactosidase or alkaline phosphatase.

15. An expression vector comprising the nucleic acid construct according to claim 10.

16. An isolated host cell comprising the nucleic acid construct of claim 10.

17. The isolated host cell of claim 16, wherein the host cell comprises a vector including the nucleic acid construct.

18. An isolated nucleic acid construct comprising:
    an enhancer which functions in a motor neuron selected from at least one of a human brain motor neuron and a spinal cord motor neuron, wherein the enhancer comprises a nucleotide sequence selected from the group consisting of SEQ ID NO: 5 and SEQ ID NO: 16;
    a basal promoter;
    a nucleic acid encoding a transcript of interest; and
    a 3' control region, wherein the enhancer, the basal promoter, the nucleic acid encoding a transcript of interest, and the 3' control region are positioned with respect to one another to permit expression of the transcript of interest.

19. The isolated nucleic acid construct of claim 18, wherein the nucleotide sequence of SEQ ID NO: 5 comprises a nucleotide sequence of SEQ ID NO: 1.

20. The isolated nucleic acid construct of claim 18, wherein the nucleotide sequence of SEQ ID NO: 5 comprises a nucleotide sequence of SEQ ID NO: 11.

21. The isolated nucleic acid construct of claim 18, wherein the transcript of interest encodes a protein selected from the group consisting of BDNF, NT-3, NT-4, erythropoietin, VEGF, IGF1, neuregulin, and CTNF.

22. An expression vector comprising the nucleic acid construct according to claim 18.

23. An isolated host cell comprising the nucleic acid construct of claim 18.

24. The isolated host cell of claim 23, wherein the nucleic acid construct is operatively positioned within an expression vector.

25. An isolated viral vector comprising the nucleic acid construct of claim 18.

26. The isolated viral vector of claim 25, wherein the viral vector is selected from the group consisting of an adenoviral vector, an adeno-associated viral vector, a lentiviral vector, and a herpes viral vector.

* * * * *

SEQUENCE LISTING

<160> NUMBER OF SEQ ID NOS: 28

<210> SEQ ID NO 1
<211> LENGTH: 438
<212> TYPE: DNA
<213> ORGANISM: Homo sapien

<400> SEQUENCE: 1

```
tgaataaatt taaggggct aattaatata taaactagcc caatttgtca agttgatttg      60
tattttagtt aattgtgaaa gtaattacca catggtcaaa ttaacagctt tctggaaatg     120
accaagcctg aggttttatt tccttcctgg gtgaagaaaa ttcattttc caagctcttg     180 atgtgatgaa taaaagtcat aaatctgggt gattggtgca ggcagagtct aaatggcttc     240
atatttcatt ttaggtttaa tagaaatatt catgctctgt tttaatgaaa ttaaattgaa     300
gggggatggg gccagagtgg ttagctgatg aattgacaaa aactaatcag ctttattggg     360
aaacaggtta agggcacggg cgtgtcaata actctcagcc tgacccctc gtccattagc      420 tcaggcaggc tgattaga                                                   438
```

```
<210> SEQ ID NO 2
<211> LENGTH: 438
<212> TYPE: DNA
<213> ORGANISM: Mus musculus

<400> SEQUENCE: 2
tgaataaatt taagcaggct aattaatata taaactagct caatttgtca agttgatttg      60
tattttagtt aattgtgaaa gtaattacca catggtcaaa ttaacagctt tctggaaatg     120
accaagcctg aggttttatt tccttcctgg gtgaagaaaa ttcattttc caagctcttg     180 atgtgatgaa taaaagtcat aaatctgggt gattggtgca ggcagagtct aaatggcttc     240
atatttcatt ttaggtttaa tagaaatatt catgctctgt tttaatgaaa ttaaattgaa     300
gggggatggg gctagagtgg ttagctgatg aattgacaaa aactaatcag ctttattggg     360
aaacaggttt aagggcacgg acgtgtcaat aacgctcagc ctgaccccct cttccattag     420
ctaggcaggc tgattaga                                                   438

<210> SEQ ID NO 3
<211> LENGTH: 438
<212> TYPE: DNA
<213> ORGANISM: Rattus norvegicus

<400> SEQUENCE: 3
tgaataaatt taagcaggct aattaatata taaactagcc caatttgtca agttgatttg      60
tattttagtt aattgtgaaa gtaattacca catggtcaaa ttaacagctt tctggaaatg     120
accaagcctg aggttttatt tccttcctgg gtgaagaaaa ttcattttc caagctcttg     180 atgtgatgaa taaaagtcat aaatctgggt gattggtgca ggcagagtct aaatggcttc     240
atatttcatt ttaggtttaa tagaaatatt catgctctgt tttaatgaaa ttaaattgaa     300
gggggatggg gccagagtag ttagctgatg aattgacaaa aactaatcag ctttattggg     360
aaacaggttt aagggcacgg gcgtgtcaat aacgctcagc ctgaccccct cttccattag     420
ctaggcaggc tgattaga                                                   438

<210> SEQ ID NO 4
<211> LENGTH: 430
<212> TYPE: DNA
<213> ORGANISM: Takifugu rubripes

<400> SEQUENCE: 4
ttcataccct ttccggaagg taattaatat ttaaactatt ccgatttgtc actttgattt      60
gtattttaga taattgtgaa tgtaattacg gagcaaatta acagctttca ggaaagaccg     120
ggttctgggg tccgggtcca tctgaggcgc cttattaatt ttctctccaa tagctgtgat     180
gaaaaggggc gataaatctg ggtgatcggt gaaggccaat actaaatggc tccatatttc     240
accgctgctt aatagaaat attcatgcgg gacaccttaa tgaaattaaa ccggcggaag     300
gcgcaagcgc gcttagttga tgaatcgaca aaaactaatc agctttattg gtagacaggt     360
taagggcaac tgggtgtcaa taattctcat tttgacctcc tcttccatta actttaagtg     420
gcttattaga                                                            430

<210> SEQ ID NO 5
<211> LENGTH: 439
<212> TYPE: DNA
<213> ORGANISM: Artificial
<220> FEATURE:
<223> OTHER INFORMATION: conserved sequence
<220> FEATURE:
<221> NAME/KEY: misc_feature
```

```
<222> LOCATION: (15)..(16)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t

<400> SEQUENCE: 5
tgaataaatt taagnnggct aattaatata taaactagcn caatttgtca agttgatttg      60
tattttagtt aattgtgaaa gtaattacca catggtcaaa ttaacagctt tctggaaatg     120
accaagcctg aggttttatt tccttcctgg gtgaagaaaa ttcattttc caagctcttg      180 atgtgatgaa taaagtcat aaatctgggt gattggtgca ggcagagtct aaatggcttc     240
atatttcatt ttaggtttaa tagaaatatt catgctctgt tttaatgaaa ttaaattgaa     300 ggggatggg gcnagagtng ttagctgatg aattgacaaa aactaatcag ctttattggg      360
aaacaggttn aagggcacgg acgtgtcaat aacnctcagc ctgaccccct cntccattag     420
ctnaggcagg ctgattaga                                                 439

<210> SEQ ID NO 6
<211> LENGTH: 313
<212> TYPE: DNA
<213> ORGANISM: Homo sapien

<400> SEQUENCE: 6
tgaataaatt taaggggct aattaatata taaactagcc caatttgtca agttgatttg      60
tattttagtt aattgtgaaa gtaattacca catggtcaaa ttaacagctt tctggaaatg     120
accaagcctg aggttttatt tccttcctgg gtgaagaaaa ttcattttc caagctcttg      180 atgtgatgaa taaagtcat aaatctgggt gattggtgca ggcagagtct aaatggcttc     240
atatttcatt ttaggtttaa tagaaatatt catgctctgt tttaatgaaa ttaaattgaa     300 ggggatggg gcc                                                        313

<210> SEQ ID NO 7
<211> LENGTH: 313
<212> TYPE: DNA
<213> ORGANISM: Mus musculus

<400> SEQUENCE: 7
tgaataaatt taagcaggct aattaatata taaactagct caatttgtca agttgatttg     60
tattttagtt aattgtgaaa gtaattacca catggtcaaa ttaacagctt tctggaaatg    120
```

```
accaagcctg aggttttatt tccttcctgg gtgaagaaaa ttcattttc caagctcttg      180 atgtgatgaa taaaagtcat aaatctgggt gattggtgca ggcagagtct aaatggcttc      240
atatttcatt ttaggtttaa tagaaatatt catgctctgt tttaatgaaa ttaaattgaa      300
gggggatggg gct                                                        313

<210> SEQ ID NO 8
<211> LENGTH: 313
<212> TYPE: DNA
<213> ORGANISM: Rattus norvegicus

<400> SEQUENCE: 8
tgaataaatt taagcaggct aattaatata taaactagcc caatttgtca agttgatttg      60
tattttagtt aattgtgaaa gtaattacca catggtcaaa ttaacagctt tctggaaatg     120
accaagcctg aggttttatt tccttcctgg gtgaagaaaa ttcattttc caagctcttg      180 atgtgatgaa taaaagtcat aaatctgggt gattggtgca ggcagagtct aaatggcttc      240
atatttcatt ttaggtttaa tagaaatatt catgctctgt tttaatgaaa ttaaattgaa      300
gggggatggg gcc                                                        313

<210> SEQ ID NO 9
<211> LENGTH: 305
<212> TYPE: DNA
<213> ORGANISM: Takifugu rubripes

<400> SEQUENCE: 9
ttcataccct ttccggaagg taattaatat ttaaactatt ccgatttgtc actttgatt      60 gtattttaga taattgtgaa tgtaattacg gagcaaatta acagcttca ggaaagaccg      120 ggttctgggg tccgggtcca tctgaggcgc cttattaatt ttctctccaa tagctgtgat      180 gaaaagggc gataaatctg ggtgatcggt gaaggccaat actaaatggc tccatatttc      240
accgctgctt aatagaaat attcatgcgg gacaccttaa tgaaattaaa ccggcggaag      300
gcgca                                                                 305

<210> SEQ ID NO 10
<211> LENGTH: 313
<212> TYPE: DNA
<213> ORGANISM: Artificial
<220> FEATURE:
<223> OTHER INFORMATION: conserved sequence
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 10
tgaataaatt taagcnggct aattaatata taaactagcn caatttgtca agttgatttg      60
tattttagtt aattgtgaaa gtaattacca catggtcaaa ttaacagctt tctggaaatg     120
accaagcctg aggttttatt tccttcctgg gtgaagaaaa ttcattttc caagctcttg      180 atgtgatgaa taaaagtcat aaatctgggt gattggtgca ggcagagtct aaatggcttc      240
atatttcatt ttaggtttaa tagaaatatt catgctctgt tttaatgaaa ttaaattgaa      300
gggggatggg gct                                                        313
```

```
<210> SEQ ID NO 11
<211> LENGTH: 125
<212> TYPE: DNA
<213> ORGANISM: Homo sapien

<400> SEQUENCE: 11
agagtggtta gctgatgaat tgacaaaaac taatcagctt tattgggaaa caggttaagg      60
gcacgggcgt gtcaataact ctcagcctga cccctcgtc cattagctca ggcaggctga     120
ttaga                                                                125

<210> SEQ ID NO 12
<211> LENGTH: 125
<212> TYPE: DNA
<213> ORGANISM: Mus musculus

<400> SEQUENCE: 12
agagtggtta gctgatgaat tgacaaaaac taatcagctt tattgggaaa caggtttaag      60
ggcacggacg tgtcaataac gctcagcctg accccctctt ccattagcta ggcaggctga    120
ttaga                                                                125

<210> SEQ ID NO 13
<211> LENGTH: 125
<212> TYPE: DNA
<213> ORGANISM: Rattus norvegicus

<400> SEQUENCE: 13
agagtagtta gctgatgaat tgacaaaaac taatcagctt tattgggaaa caggtttaag      60
ggcacgggcg tgtcaataac gctcagcctg accccctctt ccattagcta ggcaggctga    120
ttaga                                                                125

<210> SEQ ID NO 14
<211> LENGTH: 125
<212> TYPE: DNA
<213> ORGANISM: Takifugu rubripes

<400> SEQUENCE: 14
agcgcgctta gttgatgaat cgacaaaaac taatcagctt tattggtaga caggttaagg      60
gcaactgggt gtcaataatt ctcattttga cctcctcttc cattaacttt aagtggctta    120
ttaga                                                                125

<210> SEQ ID NO 15
<211> LENGTH: 125
<212> TYPE: DNA
<213> ORGANISM: Brachydanio rerio

<400> SEQUENCE: 15
agagtggtta gctgatgaat tgaggaaaac taatccgctt tattggtaga caggttaagg      60
gcaacagagt gtcaataatt ctctccctga cctctttctc cattagctta aagaggctta    120
taaga                                                                125

<210> SEQ ID NO 16
<211> LENGTH: 126
<212> TYPE: DNA
<213> ORGANISM: Artificial
<220> FEATURE:
<223> OTHER INFORMATION: consensus sequence
<220> FEATURE:
<221> NAME/KEY: misc_feature
<222> LOCATION: (68)..(68)
<223> OTHER INFORMATION: n is a, c, g, or t
```

```
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t

<400> SEQUENCE: 16
agagtggtta gctgatgaat tgacaaaaac taatcagctt tattgggaaa caggtttaag      60
ggcacggncg tgtcaataac nctcagcctg accccctcnt ccattagctn aggcaggctg     120
attaga                                                                126

<210> SEQ ID NO 17
<211> LENGTH: 36
<212> TYPE: DNA
<213> ORGANISM: Artificial
<220> FEATURE:
<223> OTHER INFORMATION: primer

<400> SEQUENCE: 17
atagcatagc ggccgctgaa taaatttaag caggct                                36

<210> SEQ ID NO 18
<211> LENGTH: 27
<212> TYPE: DNA
<213> ORGANISM: Artificial
<220> FEATURE:
<223> OTHER INFORMATION: primer

<400> SEQUENCE: 18
gctctagaag ccccatcccc cttcaat                                          27

<210> SEQ ID NO 19
<211> LENGTH: 27
<212> TYPE: DNA
<213> ORGANISM: Artificial
<220> FEATURE:
<223> OTHER INFORMATION: primer

<400> SEQUENCE: 19
gactagtaga gtggttagct gatgaat                                          27

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
tcacccgggt ctaatcagcc tgcctagct                                        29

<210> SEQ ID NO 21
<211> LENGTH: 36
<212> TYPE: DNA
<213> ORGANISM: Artificial
```

```
<220> FEATURE:
<223> OTHER INFORMATION: primer

<400> SEQUENCE: 21
atagcatagc ggccgctgaa taaatttaag caggct                              36

<210> SEQ ID NO 22
<211> LENGTH: 43
<212> TYPE: DNA
<213> ORGANISM: Artificial
<220> FEATURE:
<223> OTHER INFORMATION: primer

<400> SEQUENCE: 22
tcgttcgttt ttgtcaacgc acgagctaac cactctggct gga                     43

<210> SEQ ID NO 23
<211> LENGTH: 43
<212> TYPE: DNA
<213> ORGANISM: Artificial
<220> FEATURE:
<223> OTHER INFORMATION: primer

<400> SEQUENCE: 23
tcgtgcgttg acaaaaacga acgagcttta ttgggaaaca ggt                     43

<210> SEQ ID NO 24
<211> LENGTH: 29
<212> TYPE: DNA
<213> ORGANISM: Artificial
<220> FEATURE:
<223> OTHER INFORMATION: primer

<400> SEQUENCE: 24
tcacccgggt ctaatcagcc tgcctagct                                     29

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
cgagtgtgat catctggtcg                                               20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
ttaccttgtg gagcgacatc                                               20

<210> SEQ ID NO 27
<211> LENGTH: 40
<212> TYPE: DNA
<213> ORGANISM: Artificial
<220> FEATURE:
<223> OTHER INFORMATION: oligonucleotide probe

<400> SEQUENCE: 27
gtacgttagc tgatgaattg acaaaaacta atcagcttta                         40
```

```
<210> SEQ ID NO 28
<211> LENGTH: 40
<212> TYPE: DNA
<213> ORGANISM: Artificial
<220> FEATURE:
<223> OTHER INFORMATION: oligonucleotide probe

<400> SEQUENCE: 28
gtacgttagc tcgtgcgttg acaaaaacga acgagcttta                              40
```